(12) United States Patent
Finlay et al.

(10) Patent No.: US 10,732,171 B2
(45) Date of Patent: *Aug. 4, 2020

(54) HUMAN SKIN SAMPLE METHODS AND MODELS FOR VALIDATING HYPOTHESES FOR MECHANISMS DRIVING SKIN PIGMENTATION

(71) Applicant: The Procter & Gamble Company, Cincinnati, OH (US)

(72) Inventors: Deborah Ruth Finlay, Cincinnati, OH (US); Tomohiro Hakozaki, Cincinnati, OH (US); Charles Carson Bascom, Liberty Township, OH (US); Heather Eileen Matheny, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 415 days.

This patent is subject to a terminal disclaimer.

(21) Appl. No.: 14/367,392

(22) PCT Filed: Dec. 20, 2012

(86) PCT No.: PCT/US2012/070984
§ 371 (c)(1),
(2) Date: Jun. 20, 2014

(87) PCT Pub. No.: WO2013/096639
PCT Pub. Date: Jun. 27, 2013

(65) Prior Publication Data
US 2015/0004616 A1   Jan. 1, 2015

Related U.S. Application Data

(60) Provisional application No. 61/578,009, filed on Dec. 20, 2011.

(51) Int. Cl.
*G01N 33/50* (2006.01)
*C12Q 1/6876* (2018.01)

(52) U.S. Cl.
CPC ....... *G01N 33/5044* (2013.01); *C12Q 1/6876* (2013.01); *G01N 33/5023* (2013.01); *G01N 33/5082* (2013.01); *G01N 33/5088* (2013.01); *C12Q 2600/136* (2013.01); *G01N 2500/10* (2013.01)

(58) Field of Classification Search
None
See application file for complete search history.

(56) References Cited

U.S. PATENT DOCUMENTS

| | | |
|---|---|---|
| 5,141,741 A | 8/1992 | Ishida |
| 5,389,677 A | 2/1995 | Yu |
| 5,593,682 A | 1/1997 | Papas |
| 5,686,489 A | 11/1997 | Yu |
| D391,162 S | 2/1998 | Kokenge |
| 6,015,568 A | 1/2000 | Segot |
| 6,150,422 A | 11/2000 | Gagnebien |
| 6,294,157 B1 | 9/2001 | Rubinstenn |
| 6,589,516 B1 | 7/2003 | Eyre |
| 6,645,514 B1 | 11/2003 | Schneider |
| 6,793,929 B2 | 9/2004 | Bleckmann |
| 6,861,061 B2 | 3/2005 | Maxon |
| D516,436 S | 3/2006 | Campbell |
| D535,191 S | 1/2007 | Corker |
| 7,175,837 B2 | 2/2007 | Schiltz |
| 7,179,841 B2 | 2/2007 | Zielinski |
| D542,660 S | 5/2007 | Thomas |
| D547,193 S | 7/2007 | Blasko |
| D547,661 S | 7/2007 | Blasko |
| D558,591 S | 1/2008 | Blasko |
| D563,221 S | 3/2008 | Ashiwa |
| D570,707 S | 6/2008 | Lasko |
| 7,429,391 B2 | 9/2008 | Qu |
| 8,524,204 B2 | 9/2013 | Hakozaki |
| 8,715,628 B1 | 5/2014 | Hakozaki |
| 8,778,127 B2 | 7/2014 | Schneider |
| 2003/0091520 A1 | 5/2003 | Livoreil |
| 2003/0165546 A1 | 9/2003 | Resch |
| 2004/0009130 A1 | 1/2004 | Detore |
| 2004/0219115 A1 | 11/2004 | Kini |
| 2005/0089541 A1 | 4/2005 | Lacoutiere |

(Continued)

FOREIGN PATENT DOCUMENTS

| | | |
|---|---|---|
| DE | 103 17 400 A1 | 11/2004 |
| DE | 103 17 402 A1 | 11/2004 |

(Continued)

OTHER PUBLICATIONS

Steinstraesser et al, Open access journal of Plastic Surgery, 2009, vol. 9 pp. 27-40.*
Grizzle et al., Cancer Biomark, 2010, vol. 9, pp. 531-549.*
Baraniak et al., Regen Med, 2010, vol. 5, pp. 121-143.*
Hattori, H. et al. "The Epidermal Stem Cell Factor is Over-Expressed in Lentigo Senilis: Implication for the Mechanism of Hyperpigmentation", The Journal of Investigative Dermatology, May 5, 2004, pp. 1256-1265.
Imokawa, G. et al., "Endothelin-1 as a New Melanogen: Coordinated Expression of Its Gene and the Tyrosinase Gene in UVB-Exposed Human Epidermis", Journal of Investigative Dermatology (1995), 105, pp. 32-37.

(Continued)

Primary Examiner — Mindy G Brown
(74) Attorney, Agent, or Firm — John G. Powell

(57) ABSTRACT

Human skin tissue sample methods and models for identifying and screening test agents as effective for providing skin tone benefits, methods for validating hypotheses for mechanisms driving skin pigmentation as well as methods for driving skin pigment levels in ex-vivo skin tissue. The method includes contacting a cultured human skin tissue sample with a test agent, generating a transcriptional profile from the sample, and comparing the results to a control to determine if the test agent is effective for providing a skin tone benefit.

15 Claims, 25 Drawing Sheets

(56) References Cited

U.S. PATENT DOCUMENTS

| | | |
|---|---|---|
| 2005/0118124 A1 | 6/2005 | Reinhart |
| 2005/0169860 A1 | 8/2005 | Qu |
| 2005/0191242 A1 | 9/2005 | Brissette |
| 2006/0280709 A1 | 12/2006 | Ansmann |
| 2007/0003536 A1 | 1/2007 | Zimmerman |
| 2007/0040306 A1 | 2/2007 | Morel |
| 2007/0148664 A1* | 6/2007 | Pant et al. ............... 435/6 |
| 2007/0160550 A1 | 7/2007 | Charles Nee Newsham |
| 2007/0190190 A1 | 8/2007 | Ramirez |
| 2007/0205226 A1 | 9/2007 | Honda |
| 2008/0058281 A1 | 3/2008 | Yates |
| 2008/0108681 A1 | 5/2008 | Scimeca |
| 2009/0017080 A1 | 1/2009 | Tanner |
| 2009/0064349 A1 | 3/2009 | Goldstein |
| 2009/0068132 A1 | 3/2009 | Bratescu |
| 2009/0110709 A1 | 4/2009 | Jimenez |
| 2009/0240070 A1 | 9/2009 | Kamachi |
| 2009/0298113 A1* | 12/2009 | Vielhaber et al. .......... 435/29 |
| 2010/0029780 A1 | 2/2010 | Grayson |
| 2010/0040566 A1 | 2/2010 | Ann |
| 2011/0045477 A1 | 2/2011 | Chen |
| 2012/0148510 A1 | 6/2012 | Hakozaki |
| 2012/0156146 A1 | 6/2012 | Hakozaki |
| 2014/0335532 A1 | 11/2014 | Finlay |
| 2015/0004616 A1 | 1/2015 | Finlay |

FOREIGN PATENT DOCUMENTS

| | | |
|---|---|---|
| EP | 273202 A2 | 7/1988 |
| EP | 688559 B1 | 12/1995 |
| EP | 972508 A1 | 1/2000 |
| EP | 1053742 B1 | 11/2000 |
| EP | 1133275 A1 | 9/2001 |
| EP | 1165039 A2 | 1/2002 |
| EP | 1414404 B1 | 5/2004 |
| EP | 1525880 A1 | 4/2005 |
| EP | 2019316 A2 | 1/2009 |
| EP | 2019316 A2 | 1/2009 |
| EP | 1691199 A1 | 4/2009 |
| EP | 2124877 A2 | 12/2009 |
| EP | 2156821 A1 | 2/2010 |
| EP | 1939279 A1 | 7/2012 |
| JP | 7033639 A | 2/1995 |
| JP | 7309738 A | 11/1995 |
| JP | 8283114 A | 10/1996 |
| JP | 2000281555 A | 10/2000 |
| JP | 2001081022 A | 3/2001 |
| JP | 2003012486 A | 1/2003 |
| JP | 2003183146 A | 7/2003 |
| JP | 2003246720 A | 9/2003 |
| JP | 2007077089 A | 3/2007 |
| JP | 2011130751 A | 7/2011 |
| JP | A-2011-130751 | 7/2011 |
| WO | WO1998034591 A1 | 8/1998 |
| WO | WO2000078272 A3 | 8/2001 |
| WO | WO2004066973 A1 | 8/2004 |
| WO | WO2008022834 A1 | 2/2008 |
| WO | WO2009067095 A1 | 5/2009 |
| WO | WO2009105294 A2 | 8/2009 |
| WO | WO2011/022451 A1 | 2/2011 |

OTHER PUBLICATIONS

IPRP; PCT/US2012/070993; International Filing Date Dec. 20, 2012.
IPRP; PCT/US2012/070993; Date of Mailing Jul. 3, 2014.
International Search Report PCT/US2012/070993; dated Mar. 7, 2013.
International Search Report PCT/US2012/070984; dated Mar. 5, 2013.
Lehe, CL et al. "A Two-centre Evaluation of the Human Organotypic Skin Explant Culture Model for Screening Contact Allergens" Alternatives to Laboratory Animals, 2003, vol. 31, No. 6, pp. 553-561.

* cited by examiner

Topical application of Niacinamide in formulation vs its vehicle control

Fitzpatric Score 3

| Donor #1 | Niacinamide 5% |
|---|---|
| POMC | -1.74 |
| MC1R | -1.83 |
| MITF | 1.23 |
| TYR | -2.28 |
| TYRP1 | -1.98 |
| DCT | -2.04 |
| TGFB1 | -1.09 |
| EDN1 | -1.09 |

Fitzpatric Score 3

| Donor #2 | Niacinamide 5% |
|---|---|
| POMC | -4.45 |
| MC1R | -3.34 |
| MITF | -1.68 |
| TYR | -1.62 |
| TYRP1 | 1.17 |
| DCT | -1.30 |
| TGFB1 | -7.08 |
| EDN1 | -2.54 |

Fitzpatric Score 5

| Donor #3 | Niacinamide 5% | Niacinamide 7.5% |
|---|---|---|
| POMC | 1.00 | -1.36 |
| MC1R | 1.14 | -1.53 |
| MITF | -1.11 | -1.37 |
| TYR | -1.26 | -1.51 |
| TYRP1 | -1.07 | -1.26 |
| DCT | -1.23 | -1.86 |
| TGFB1 | -1.17 | -1.32 |
| EDN1 | 1.02 | -1.42 |

Fold Regulation (comparing to vehicle control)

| | |
|---|---|
| Up reg | p≤0.05 |
| Up reg | p≤0.10 |
| Down reg | p≤0.05 |
| Down reg | p≤0.10 |

Fig. 1

Tone gene regulation over time in untreated skin of Fitz 3 vs Fitz 5

| Up-Down Regulation (comparing to control group) | | | | | |
|---|---|---|---|---|---|
| Inflammation Genes | | | | | |
| against 24hr | 48hrs | 72hrs | 96hrs | 6day | 8day |
| IL8 | -1.08 | 1.20 | 1.22 | 2.43 | 2.36 |
| IL6 | -1.03 | -1.72 | -1.00 | 1.54 | 1.45 |
| TNF | 1.98 | 2.11 | 2.57 | 3.80 | 2.16 |

| Tone Genes | | | | | |
|---|---|---|---|---|---|
| | 48hrs | 72hrs | 96hrs | 6day | 8day |
| POMC | 3.53 | 2.00 | 3.97 | 5.16 | 2.60 |
| MCR1 | 2.28 | 1.46 | 2.57 | 3.72 | 2.06 |
| MITF | 1.66 | 1.13 | 2.01 | 3.64 | 1.57 |
| TYR | 2.06 | 2.16 | 1.84 | 3.48 | 1.37 |
| TYRP1 | 1.23 | -1.33 | 1.44 | 3.23 | 1.43 |
| DCT | 1.34 | -1.01 | 2.06 | 4.23 | 1.38 |
| TGFB1 | 1.27 | 1.00 | -1.08 | 1.88 | -1.06 |
| EDN1 | 1.29 | 1.04 | 1.80 | 3.34 | 1.28 |

| | |
|---|---|
| Up reg | p≤0.05 |
| Up reg | p≤0.10 |
| Down reg | p≤0.05 |
| Down reg | p≤0.10 |

Fig. 5

4 day time point

| gene | Niacina-mide 0.1% (media) | Niacina-mide 0.2% (media) |
|---|---|---|
| POMC | 2.16 | 4.60 |
| MC1R | 2.08 | 3.78 |
| MITF | 2.31 | 2.22 |
| TYR | 2.41 | 3.34 |
| TYRP1 | 2.62 | 1.70 |
| DCT | 2.67 | 3.12 |
| TGFB1 | 1.12 | 1.32 |
| EDN1 | 1.93 | 1.70 |

Up-Down Regulation (comparing to untreated)

7 day time point

| gene | Niacina-mide 0.1% (media) | Niacina-mide 0.2% (media) |
|---|---|---|
| POMC | -1.37 | -1.29 |
| MC1R | -1.22 | -1.12 |
| MITF | -1.69 | -1.45 |
| TYR | -2.61 | -2.32 |
| TYRP1 | -1.17 | -1.30 |
| DCT | -1.07 | -1.06 |
| TGFB1 | 1.40 | 1.10 |
| EDN1 | -1.41 | -1.19 |

Up-Down Regulation (comparing to untreated)

| Up reg | p≤0.05 |
|---|---|
| Up reg | p≤0.10 |
| Down reg | p≤0.05 |
| Down reg | p≤0.10 |

Days in culture at 50% humidity and 37 degrees C

| Mostly Epidermal | POMC | propiomelancortin |
|---|---|---|
| | MC1R | Melanocortin 1 receptor |
| | MITF | Microphthalmia-associated transcription factor |
| | TYR | Tryosinase |
| | TYRP1 | tyrosinase related protein 1 |
| | DCT | dopachrome tautomerase (TYRP2) |
| | TGFB1 | transforming growth factor 1 |
| | EDN1 | Endothelin 1 |
| Mostly Dermal and tissue health | LEF1 | Lymphoid enhancer binding 1 factor |
| | FGF2 | Fibroblast growth factor |
| | KIT | v-kit |
| | EDNRB | Endothelin receptor type B |
| | HGF | Hepatocyte growth factor |
| | BCL2 | B-cell CLL/lymphoma 2 |
| | BAX | BCL-2 associated protein |
| House-keeping genes | 18srRNA | Human 18s Ribosomal RNA |
| | ACTB | Beta Actin |
| | GAPDH | Glyceraldehyde-3-phosphaste dehyrdogenase |
| | PPIA | Peptidylpropylisomerase A (cyclophylinA) |

Fig. 10

| HEX 1 | HEX 0.001% | HEX 0.01% |
|---|---|---|
| POMC | -2.12 | -2.83 |
| MC1R | -1.44 | -2.35 |
| MITF | -1.82 | -3.19 |
| TYR | -1.78 | -4.14 |
| TYRP1 | -1.67 | -1.89 |
| DCT | -1.56 | -1.99 |
| TGFB1 | -1.37 | -1.81 |
| EDN1 | -2.07 | -3.51 |

| | |
|---|---|
| Up reg | p≤0.05 |
| Up reg | p≤0.10 |
| Down reg | p≤0.05 |
| Down reg | p≤0.10 |

| Fold regcompared to vehicle-endogenous | | |
|---|---|---|
| | Kojic Acid | Transhexamic Acid |
| POMC | -1.8989 | -4.8999 |
| MC1R | -7.5981 | -12.8891 |
| MITF | -2.4053 | -2.6609 |
| TYR | -1.3292 | -2.0247 |
| TYRP1 | -1.3233 | -1.0569 |
| DCT | -1.0766 | -1.5122 |
| TGFB1 | -1.4907 | -6.4205 |
| EDN1 | -1.5532 | -2.6376 |

| | |
|---|---|
| Up reg | p≤0.05 |
| Up reg | p≤0.10 |
| Down reg | p≤0.05 |
| Down reg | p≤0.10 |

|  | HEX 0.001% + SE | HEX 0.01% + SE |
|---|---|---|
| POMC | -1.5175 | -2.5944 |
| MC1R | 1.2209 | -1.5632 |
| MITF | 1.7925 | -1.2212 |
| TYR | 1.1734 | -2.0091 |
| TYRP1 | 1.3605 | 1.1669 |
| DCT | 1.2286 | -1.1679 |
| TGFB1 | 1.2618 | -1.5208 |
| EDN1 | 1.0466 | -2.6248 |

| | |
|---|---|
| Up reg | p≤0.05 |
| Up reg | p≤0.10 |
| Down reg | p≤0.05 |
| Down reg | p≤0.10 |

| | Niacinamide 0.25% + SE |
|---|---|
| POMC | -1.5145 |
| MC1R | -1.9573 |
| MITF | 1.6182 |
| TYR | -1.3851 |
| TYRP1 | -2.7944 |
| DCT | -1.2288 |
| TGFB1 | -1.1535 |
| EDN1 | 1.2231 |

| | |
|---|---|
| Up reg | p≤0.05 |
| Up reg | p≤0.10 |
| Down reg | p≤0.05 |
| Down reg | p≤0.10 |

| | SE + Nag 5% (Added at Day 4) |
|---|---|
| POMC | 1.352 |
| MC1R | 1.7479 |
| MITF | 1.495 |
| TYR | -2.2836 |
| TYRP1 | -1.27 |
| DCT | 1.1586 |
| TGFB1 | 1.0591 |
| EDN1 | 1.1399 |

| | |
|---|---|
| Up reg | p≤0.05 |
| Up reg | p≤0.10 |
| Down reg | p≤0.05 |
| Down reg | p≤0.10 |

| 10/27/2009 | Hexyldecanol 5% |
|---|---|
| POMC | -2.35 |
| MC1R | -3.05 |
| MITF | -2.45 |
| TYR | -2.37 |
| TYRP1 | -1.86 |
| DCT | -2.04 |
| TGFB1 | -1.81 |
| EDN1 | -3.11 |

Fig. 25A

| 11/12/2009 | Hexyldecanol 5% |
|---|---|
| POMC | -6.46 |
| MC1R | -6.08 |
| MITF | -2.31 |
| TYR | -3.12 |
| TYRP1 | -1.07 |
| DCT | -2.56 |
| TGFB1 | -1.14 |
| EDN1 | -4.57 |

$p \leq 0.05$
$p \leq 0.1$

Fig. 25B

HUMAN SKIN SAMPLE METHODS AND MODELS FOR VALIDATING HYPOTHESES FOR MECHANISMS DRIVING SKIN PIGMENTATION

TECHNICAL FIELD

One aspect of the invention relates to novel ex-vivo skin models and screening methods for identifying tone agents that may be suitable for use in cosmetic compositions. Another aspect of the invention relates to methods for using an ex-vivo model for driving a pigment level in ex-vivo skin samples.

BACKGROUND OF THE INVENTION

Skin pigmentation levels and regulation are determined and controlled by a complex system of interrelated genes, proteins and a milieu of intracellular and extracellular compounds, some of which have yet to be elucidated. Skin models capable of mimicking aspects of cellular processes integral to the skin pigmentation pathway(s) are therefore desired in order, for example, to identify skin-active agents effective in modulating skin pigmentation.

Modeling techniques to study skin physiology and skin responses to agents have historically included a variety of specific techniques, from the culturing of a single cell type or a small number of co-mingled cell types, to fabricating human tissue equivalents, to developing animal models. However these relatively simple models often lack much of the intra and intercellular complexities of human skin. For example, cell cultures of single cell types are easily utilized but overly simplistic and have severe limitations for generalizing results to human skin. First, such cultures contain cells that are altered simply by being cultured and, in specific cases, have been altered by genetic manipulation to promote easy cell passaging and maintenance. Second, such cultures cannot account for intrinsic intricate matrices of cells constantly interacting as a unit. Multi-celled cultures are limited due to difficulties in creating the integrated mechanical structure of native tissue and in ensuring that the cells comprise the extracellular components necessary to maintain cellular genetic expression levels at a normal physiological level. Models that include stem cells treated to mimic human skin are suitable for their intended purposes, but fall victim to similar concerns and limitations.

More complex skin models include animal models and skin-equivalent models. While having additional complexity, animal models suffer from limitations including the genetic variation with respect to human skin; in the analysis of obtained results there is always a concern that human tissues react differently from animal tissues and the ability to generalize results is compromised. For example, animal models of skin may differ substantially from human skin, in natural pigment levels or in the ability to up-regulate specific genes. Additionally, even slight variations in receptor levels can lead to responses that are less, more, or seemingly idiosyncratic in relation to what might be seen in human skin responses depending on whether the tested agent binds with different kinetics or not at all, or in such a way as to activate or inactivate various alternative internal pathways or genes. In addition, extrinsic factors can affect test results with animals, and stressors unrelated to the test agent could also affect results.

Skin-equivalent models are limited by lack of cellular interconnectivity, permeability concerns, and anatomical simplicity. More recent attempts at skin-equivalent models may be described as organotypic human tissue equivalents and include in vitro reconstructions of human cells such as keratinocytes cultured on an inert polycarbonate filter. These models by their very nature are limited in that they can have reduced barrier function that can lead to aberrant sensitivities to tested agents. The models also are less complex than human skin, having perhaps one or two cells types (such as keratinocytes and fibroblasts or keratinocytes and melanocytes) but lacking additional cells such as endothelial cells or even the full keratinocyte, fibroblast, and melanocyte combination. In addition the organotypic skin equivalent models are also missing normal skin structures such as glands that can affect skin response.

The most complex skin model involves the ex vivo culture of human skin tissue samples. Previous attempts to utilize ex-vivo human skin as an assay model had limitations such as brief life-spans with low vitality or viability. Previous attempts at such models included small biopsies of skin floating directly in media, which is not analogous to the normal environment of the skin and resulted in the tissue having a limited lifespan. It is known in the art that transient cultures can be deficient, as inventors and researchers have indicated attempts at ex-vivo pig skin grafts are limited to seven days (Vielhaber et al., Ex vivo Human Skin Model, US2009/0298113).

Even more recent ex-vivo models have involved attempting to culture skin explants on metal grids (Mitts et al., Elastin Protective Polyphenolics and Methods of Using the Same, US2009/0110709) and skin grafting to the chorioallantoic membrane (CAM) of a fertilized ovarian egg (Goldstein et al., Chimeric Avian-Based Screening System Containing Mammalian Grafts, US2009/0064349). However such models are still limited by transiency of the construct, delicacy, and even xenogeneic concerns. One attempt at improving the longevity of ex-vivo skin is described in EP 2 019 316 B1.

Despite these advancements, a need continues to exist for a sensitive and predictive ex-vivo human skin tissue screening method that is robust enough to manage inherent donor-to-donor tissue variability, is stable over a sufficient time period to identify both weak and strong tone agents, and is predictive based upon an analysis of the gene transcriptomics of the donor tissue. The latter is particularly useful in a low through-put screening method for tone agents, as measuring gene transcriptomics is relatively quick and fold changes are reliably ascertainable over shorter time periods more than other end points, such as measuring the amount of melanin produced or inhibited in the ex-vivo tissue sample.

As discussed more fully hereafter, the challenges and uncertainties associated with developing a practical screening method for tone agents are numerous. Non-limiting examples include: the effect of donor to donor skin type variability, the effect of donor to donor skin status variability (e.g., the state of inflammation and viability) post surgical extraction, whether culturing conditions could establish viability of the tissue samples for sufficient periods of time to assess both slow and fast acting tone agents, whether ex-vivo skin tissue can be properly regulated at the gene transcriptomic level over the needed time periods, whether analysis of gene transcriptomics of ex-vivo skin tissue could be predictive of in vivo results, whether appropriate positive controls could be identified for use in a high enough percentage of the tissue samples to develop a satisfactory screening method, and whether these variables could be controlled to the point that the effects of a tone agent on an ex-vivo skin tissue sample could be isolated and interpreted so as to be repeatable to a level of statistical significance.

SUMMARY

Accordingly, the present investigators have developed an ex-vivo human skin model and screening methods that can be used for tone-specific responses and that addresses one or more of these challenges and uncertainties.

In accordance with various embodiments disclosed herein, methods for identifying an agent as effective for providing a skin tone (for example, lightening) benefit are provided. According to one embodiment, the method comprises culturing a first human skin tissue sample, wherein the first human skin tissue sample comprises an epidermal layer and a dermal layer; contacting the human skin tissue sample with the at least one test agent; generating a transcriptional profile from the first human skin tissue sample, wherein the transcriptional profile comprises data related to transcription of at least two genes selected from FIG. 10; and identifying the at least one test agent as effective for providing a skin tone benefit when the at least two genes selected from FIG. 10 show a directionally appropriate increase or decrease in expression level in comparison to an untreated control tissue sample.

In accordance with additional embodiments disclosed herein, methods for preparing ex-vivo skin tissue for use in a screening method are provided. According to one embodiment the method comprises: providing an adult human skin tissue sample; removing a subcutaneous fat layer from the adult human skin tissue sample; trimming the adult human skin sample to a uniform size; storing the adult human skin sample at between about two degrees Celsius and about six degrees Celsius; and wherein the adult human skin tissue sample is from a donor rated between about 2 and about 4 on the Fitzpatrick Scale.

Additional embodiments disclosed herein provide methods of validating a hypothesis about particular mechanisms driving skin pigmentation. According to one embodiment, a method comprises: identifying at least one candidate agent for driving skin pigmentation; hypothesizing that the at least one candidate agent drives skin pigmentation; providing a cultured human skin tissue sample for a period of time under suitable conditions to test the effectiveness of at least one candidate agent for driving skin pigmentation; wherein the human skin tissue sample comprises an epidermal layer and a dermal layer; contacting the human skin tissue sample with the at least one candidate agent during the period of time; generating a transcriptional profile from the treated human skin tissue sample, wherein the transcriptional profile comprises data related to transcription of at least two genes selected from FIG. 10; and validating the hypothesis that the at least one candidate agent drives skin pigmentation when all of the at least two genes selected from FIG. 10 are at least one of increased in expression level in comparison to an untreated control tissue sample or all of the at least two genes selected from FIG. 10 are decreased in expression level in comparison with an untreated control tissue sample.

Additional embodiments provide methods for identifying drivers (stimulators) of a pigment level in ex-vivo skin tissue. According to one embodiment, a method comprises: driving (stimulating) a pigment level in ex-vivo skin tissue, comprising: culturing a human skin tissue sample; wherein the human skin tissue sample comprises an epidermal layer and a dermal layer; contacting the human skin tissue sample with at least one agent selected from the control group consisting of Endothelin 1, Stem Cell Factor, Melanocyte Stimulating Hormone, Forskolin, or ultraviolet light which up-regulate the pigmentation machinery of the cell; and assaying for the effect of an unknown to, similarly, up-regulate pigmentation.

BRIEF DESCRIPTION OF THE FIGURES

FIG. 1 illustrates the fold regulation change, relative to a vehicle control, of certain genes in two Fitzpatrick III tissue samples using 5% niacinamide and one Fitzpatrick V tissue sample using 5% niacinamide and 7.5% niacinamide.

FIG. 5 is a heat map illustrating the fold change for certain inflammation and tone genes for a Fitzpatick III tissue sample over a time course of 8 days.

FIG. 6 is a heat map illustrating the fold regulation change for certain tone genes at 4 days and 7 days compared to an untreated control.

FIG. 10 is a table setting forth specific non-limiting tone genes for which, in specific embodiments, a transcriptional analysis may be conducted.

FIGS. 25a and 25b show two respective tables showing ex-vivo model fold regulation changes indicating significant down-regulation by clinical formulations in the Human Ex-vivo Pre-Clinical Model.

DETAILED DESCRIPTION

Figure 2A:
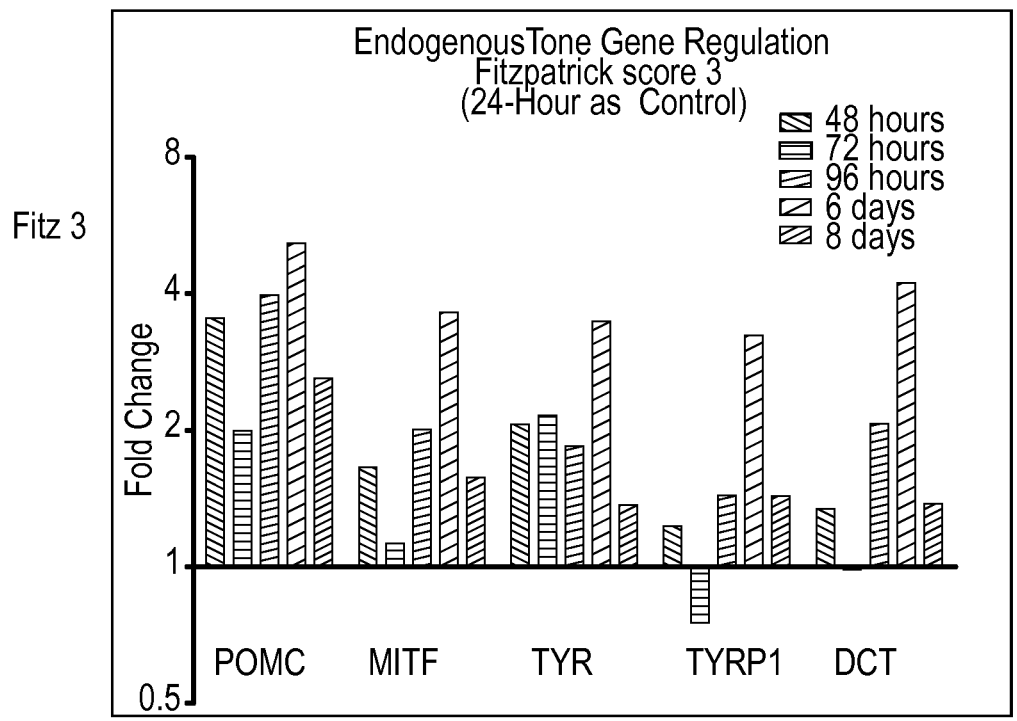
FIG. 2A illustrates the fold change for certain genes of an untreated Fitzpatrick III tissue sample over 8 days relative to a 24 hour control.

The present investigators have developed an ex-vivo human skin model and screening methods that can be used to measure tone-specific responses and overcome the challenges and uncertainties of current technology. For clarification, specific, non-limiting embodiments of the invention are herein described. The skilled artisan will readily appreciate that the devices and methods herein are merely exemplary and that variations can be made without departing from the spirit and scope of the invention. It is also to be understood that the terminology used herein is for the purpose of describing particular embodiments only and is not intended to be limiting. As used in the description of the invention and appended claims, the singular "a," "an," and "the" are intended to include the plural forms as well, unless the context clearly indicates otherwise.

Unless otherwise defined, all technical and scientific terms used herein have the same meaning as commonly understood by one of ordinary skill in the art to which this invention pertains. The terminology used in the description of the invention herein is for describing the particular embodiments only and is not intended to be limiting of the invention.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Non-limiting aspects and examples of various embodiments of ex-vivo skin screening methods will now be described. While various embodiments are described hereafter in the context of controls, culturing conditions, gene transcriptomics, processing of skin tissue, mRNA processing, it will be appreciated that the details provided herein are intended to be illustrative only and that many modifications, additions, deletions, and other changes are possible in view of the teachings herein.

The ex-vivo skin screening methods/assays generally comprise one or more of the following: collecting surgical waste donor tissue, preparing the tissue for culturing, treating the tissue with test material applied topically or within the culture medium, culturing the tissue for a specified period of time, and measuring one or more endpoints of interest (e.g., gene transcription, etc.). A non-limiting description of these various aspects follows.

I. Donor Tissue

Figure 2B:
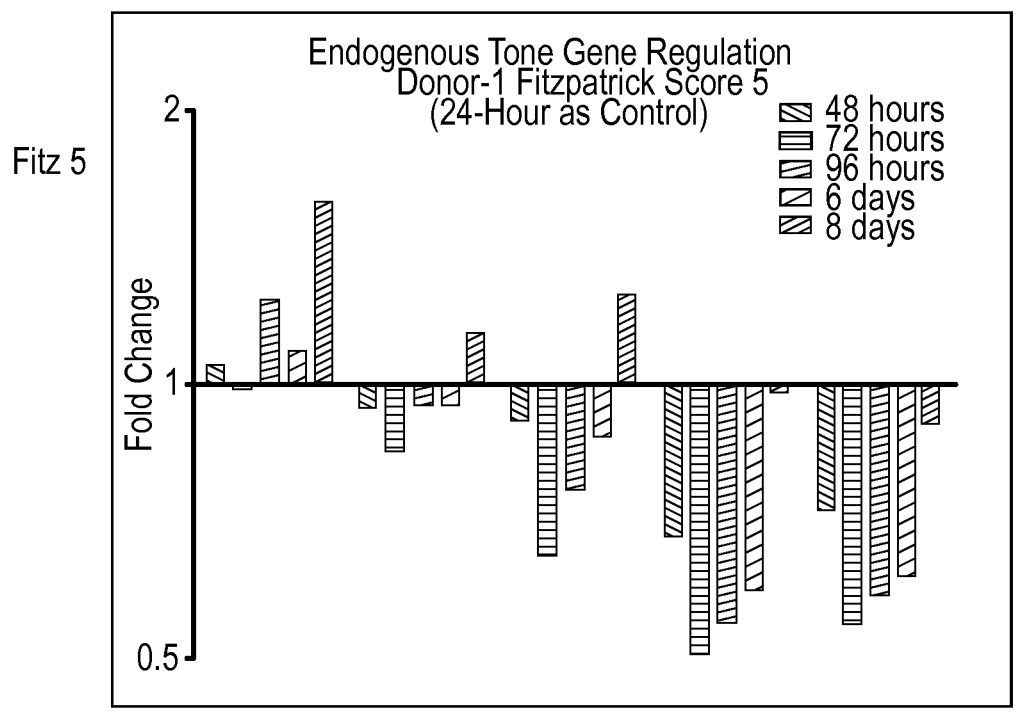
FIG. 2B illustrates the fold change of certain genes for an untreated Fitzpatrick V tissue sample over 8 days relative to a 24 hour control.

Donor tissue samples may be surgical waste tissue from any of a wide variety of procedures, including but not limited to abdominoplasty or full body lift procedures. One aspect discovered by the investigators is the desirability of limiting the tissue samples to certain Fitzpatrick scores. In specific embodiments, it may be desirable to use donor tissue samples having a Fitzpatrick score between II and IV or even having a score that is either II or III in the screening method. Fitzpatrick score is a numerical classification schema for the color of skin. Type I is very fair; Type II is fair; Type III is beige; Type IV is beige with brown tint; Type V is dark brown, and Type VI is black. The investigators have found that Type I skin does not produce enough eumelanin (pigment) to provide reliable transcriptomic data for the pigmentation genes of interest, and higher Fitzpatrick scores, while they can be used, seem to introduce higher variability into the assay with respect to pigmentation genes influenced by stress/inflammation. For example, a Type V might respond well to a positive control at a concentration of 7.5% (meaning the genes of interest are properly regulated by the positive control) while this concentration of the active might be toxic for Types II and III. This might be due to the observation of the investigators that the darker skin tissues are less stressed post surgery and able therefore to tolerate the stress introduced by the higher concentration of a positive control due to greater on board melanin concentrations that act as excellent antioxidant protection. Also, the investigators observed in at least one Type V tissue sample that the tone genes of interest were down-regulated instead of up-regulated (possibly indicating less stress in the overall tissue), indicating additional undesirable variability associated with Type V skin samples. Referring to FIG. 1, it can be seen that it is more challenging to down-regulate, with statistical significance, a Fitzpatrick V donor with 5% niacinamide than two Fitzpatrick III donors at the same concentration of niacinamide. Referring to FIG. 2, a comparison is illustrated between an untreated Fitzpatrick III donor and an untreated Fitzpatrick V donor. As can be seen in FIG. 2, the pigmentation genes of the Fitzpatrick III donor were more consistently up-regulated across the time periods than in the Fitzpatrick V donor.

Upon receipt, the tissue may be stored at a temperature below room temperature, such as between about 2° C. and about 10° C. or from about 2° C. and about 6° C. for up to about 24 hours.

The investigators have found that storage at cooler temperatures can pause development of inflammation, which will resume upon tissue re-warming.

Figure 3A:
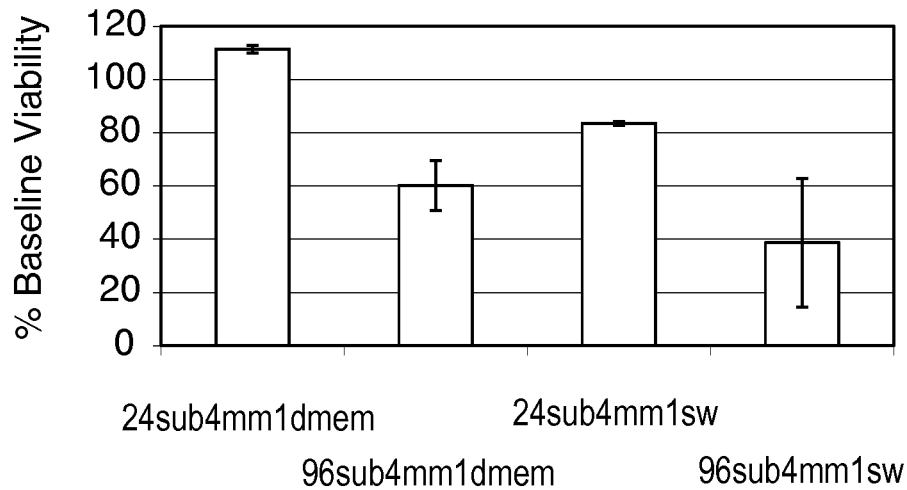
FIG. 3A is a bar graph illustrating the viability of ex-vivo skin tissue, as assessed in an MTT assay (3-(4,5-Dimethylthiazol-2-yl)-2,5-diphenyltetrazolium bromide assay), for a 4 mm punch of the skin tissue cultured directly in DMEM.
Figure 3B:
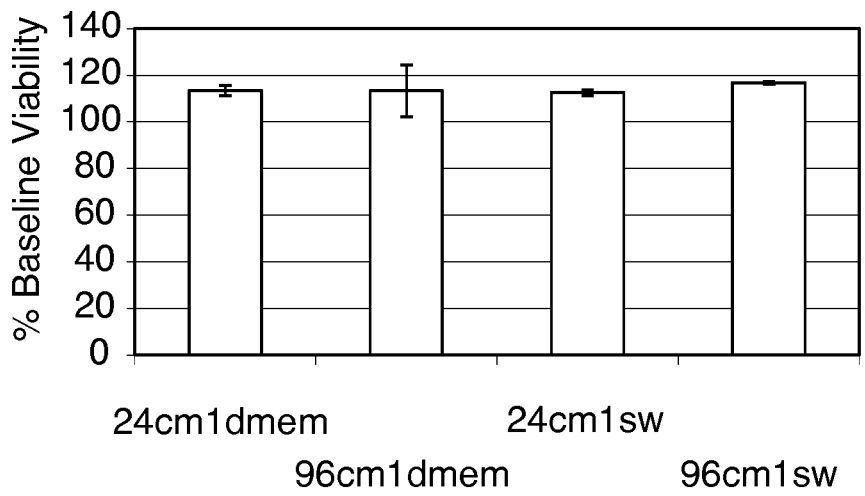
FIG. 3B is a bar graph illustrating the viability of ex-vivo tissue skin, as assessed in an MTT assay for a 1 cm sample cultured on a membrane in DMEM and SW media.

The tissue sample may then be trimmed to remove the subcutaneous layer. Removal of the fat layer can improve absorption of the media into the tissue during culturing. Trimming the fat layer also enables a tissue model that is suitable for either topical or media delivery of test agents. The tissue sample may then be further subdivided into smaller pieces (e.g., 1.25 mm×1.25 mm square) which are placed into a multi-well tissue plate. In specific embodiments, each of the smaller pieces is placed on a membrane (e.g., a Millipore, eight micron, six-well membrane insert) within the wells. Use of a membrane can significantly improve the viability of the tissue sample during culturing. This is shown in FIGS. 3A and 3B, where a comparison is illustrated between 4 mm ex-vivo skin punches cultured in a media and 1 cm pieces ex-vivo skin samples cultured on a membrane. At 96 hours, there is a marked decrease in viability of the 4 mm punches versus the 1 cm samples.

The tissue samples may be positioned in the plate wells with the dermis side down over an iso-osmotic solution to keep the dermis moist and the epidermis dry. The iso-osmotic (or isotonic) solution can be Dulbecco's Modified Eagle Medium (DMEM). Additionally, the tissue samples can be placed in non-osmotic (non-isotonic) solution. Any of the solutions can have optionally anti-mycotic or antibacterial reagents within them or provided to tissue separately.

II. Culturing Conditions: Temperature, Time, Humidity

The investigators have found that ex-vivo tissue culturing conditions, including one or more of temperature, time, and humidity, can affect several relevant aspects of an ex-vivo skin screening method for tone agents. First, with regard to temperature, the investigators have found that culturing temperature influences the amount of endogenous inflammation (which can affect the amount of initial up-regulation of the tone genes of interest) in the donor tissue. Second, the investigators have found that the amount of time it can take for a positive control and/or weaker tone agents to down-regulate the tone genes of interest can vary, which in turn impacts how long or short the culturing time period should be. Third, the investigators have found that humidity can affect tissue viability and that decreasing the humidity level can provide flexibility to increase the culturing temperature without unduly impacting tissue viability and/or the level endogenous inflammation.

Temperature

In an endogenously regulated tissue sample (meaning no compounds are applied to the tissue with the specific intent of up-regulating the tone genes of interest), the donor tissue samples should have a sufficient level of endogenous inflammation to result in up-regulation of the tone genes of interest so that down-regulation of the genes by a test compound can be observed. The amount of up-regulation should be sufficient to account for donor to donor variability, meaning a robust screening method should utilize culturing conditions that cause a sufficient amount of up-regulation of the tone genes of interest across a wide donor population. This enables a consistent determination as to whether a test compound is capable of down-regulating the tone genes (as do the positive controls). However, confoundingly, the investigators have observed that if the donor tissue is too strongly up-regulated, it is possible that weaker tone agents and/or positive controls may not be able to down-regulate the tone genes consistently across a sufficient portion of the population of donors. The investigators have also found that temperature selection can also be a function of the humidity level (e.g., the lower the humidity, the higher the temperature that may be tolerated by the tissue sample while remaining viable).

Figure 4A:
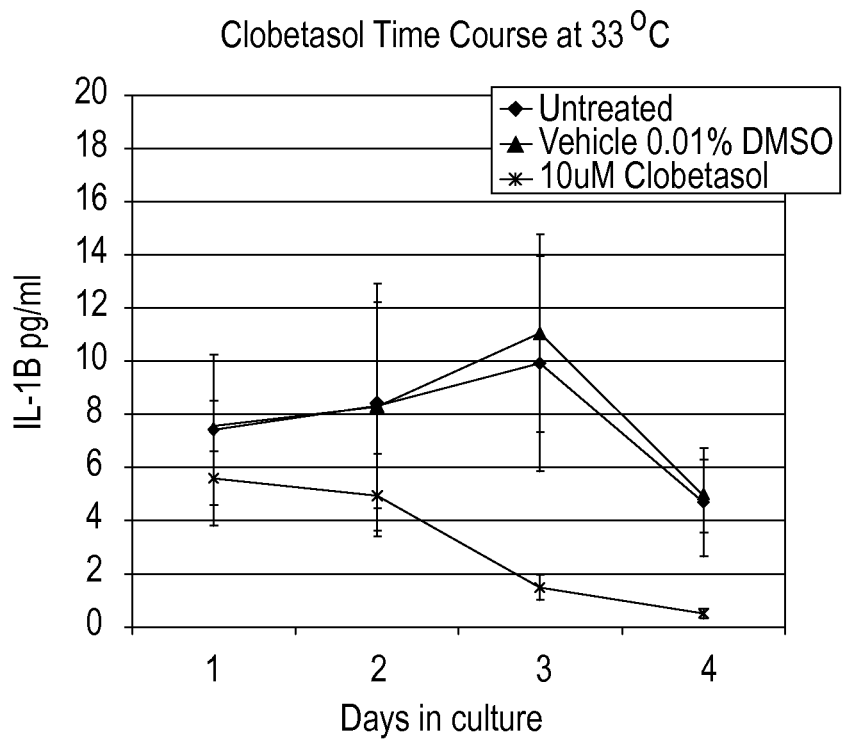
FIG. 4A is a graph of IL-1 beta cytokine released into the media by tissue at 33 Celsius.
Figure 4B:
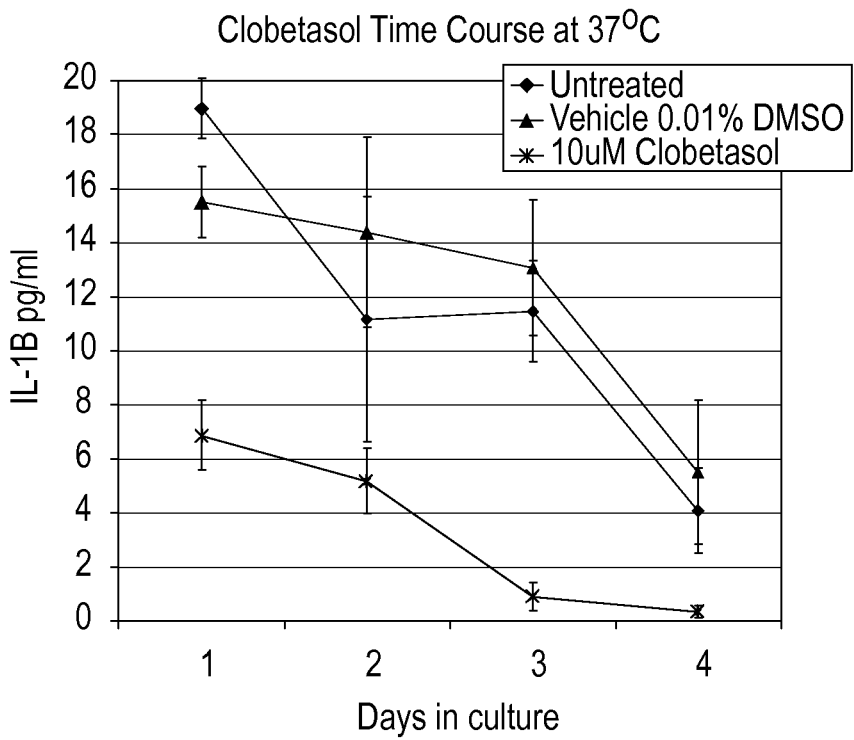
FIG. 4B is a graph if IL-1 beta cytokine released into the media by tissue at 37 Celsius.

Generally, the higher the culturing temperature, the greater the state of inflammation of the tissue sample. For example, as shown in FIGS. 4A (33° C.) and 4B (37° C.), it can be seen that as temperature increases (from 33° C. to 37° C.) IL-1 beta cytokine release increases (investigators have noted that prior to culturing, tissue samples can be stored at 2° C.-10° C.). The total IL-1 beta cytokine release and pattern of release were different at different temperatures (release was 2× higher at 37° C. than at 33° C. at the earlier time points). The investigators have discovered that the higher the state of inflammation in an ex-vivo tissue sample, the more that the tone genes of interest are correspondingly up-regulated. For example, FIG. 5 shows tissue that is cultured and analyzed over the course of 8 days (untreated). In FIG. 5, it can be seen that as inflammation genes (IL-8, IL-6, and TNF) in Fitzpatrick III donor tissue are up-regulated so too are the tone genes of interest (e.g., POMC, MC1R, MITF, TYR, TYRP1, DCT, TGFB1, EDN1, and SLC11A2). Interestingly, the investigators did not observe the same regulation in at least one Type V tissue donor. Thus, the investigators have demonstrated a correlation between the state of inflammation of the ex-vivo tissue sample and the up-regulation of the tone genes of interest. This correlation is significant, because it means that it's possible to have sufficient up-regulation of the tone genes endogenously across a large donor population.

Based on the foregoing considerations, in specific embodiments, the culturing temperature for the ex-vivo skin tissue is from about 30° C. to about 40° C. or from about 33° C. to about 37° C. These temperature ranges enable culturing tissue samples that have rather consistent and sufficient levels of endogenous inflammation as well as tissue viability for use in the screening methods. The success at near the 37 degrees Celsius is unexpected as the body temperature of the exterior of the skin would be below this, as human skin is exposed to much lower temperatures in various cases. Additionally, the 33 degree mark slows metabolism and would provide a much lower temperature than the skin normally experiences. It will be appreciated however that the culturing temperature can be further increased or decreased beyond these ranges as a function of observed tissue toxicity, the desired level of endogenous inflammation, humidity level, and desired culturing time.

Time

A robust ex-vivo skin assay/screening method for tone agents should be (although does not necessarily need to be) sensitive enough to identify strong tone agents (which may influence the regulation of the genes of interest over a short period of time) and weaker tone agents (which may require longer periods of time to influence an observable regulation of the genes of interest). For example, certain weaker tone agents may not provide a reliable and sufficient down regulation of the tone genes of interest until between at 5 and 10 days, or longer. Ideally, the tissue samples should be viable over a culturing time period sufficient to identify weaker tone agents. In addition, the donor tissue should be viable over the time period necessary for the positive controls to show proper regulation of the tone genes over a majority of the donor population. Relatedly, the donor tissue population should show generally consistent regulation of the genes of interest during the selected time period. The longer the time period, the more likely this is to be the case.

The investigators have selected, tested and analyzed a number of potential positive controls, including niacinamide, undecylenoyl phenylalanine, hexamidine, tranexamic acid, kojic acid, and N-acetyl glucosamine. Referring to FIG. 6, the investigators have found that a culturing time period greater than 4 days, and preferably greater than 6 days, is desirable with respect to niacinamide to show consistent down regulation of the tone genes against endogenous inflammation across a donor population. The investigators have in certain embodiments found consistency in culturing time periods of 24 hours to 7 days for various benchmarks. Certain positive controls may respond more quickly, such as undecylenoyl phenylalanine, while other positive controls may need to be even longer. Thus, the period of time in various cases can be from 24 hours to 14 days or more. In certain exemplary cases the period of time is 6-8 days. In certain cases where agents prove severely stressful to the tissue or decrease overall tissue viability or are highly active or effective, the time course can be shortened or levels of dose response can be created (or both) so as to obtain effective and meaningful results. For example, in these instances the time may be 24 to 28 hours.

Humidity

The investigators found surprisingly that the longevity of the cultures could be maintained for much longer periods of time and with great consistency of results under unique conditions; for example conditions of reduced humidity. This can be useful where, as discussed above, it may be necessary to culture for an extended period of time to identify weaker tone agents and/or provide a sufficient amount of time for appropriate and consistent regulation of the tone genes of interest by the positive control. In addition, by decreasing humidity the investigators have found that it is possible to culture at otherwise higher temperatures while still maintaining tissue viability and consistent gene regulation. Specifically, regarding humidity, the current investigators found surprisingly that the longevity of the cultures could be maintained for much longer periods of time in conditions of reduced humidity. Standard culture techniques tend to have very high humidity, reaching upwards of 95%. The investigators found that reducing the humidity had a profound effect on skin sample viability.

Figure 7A:
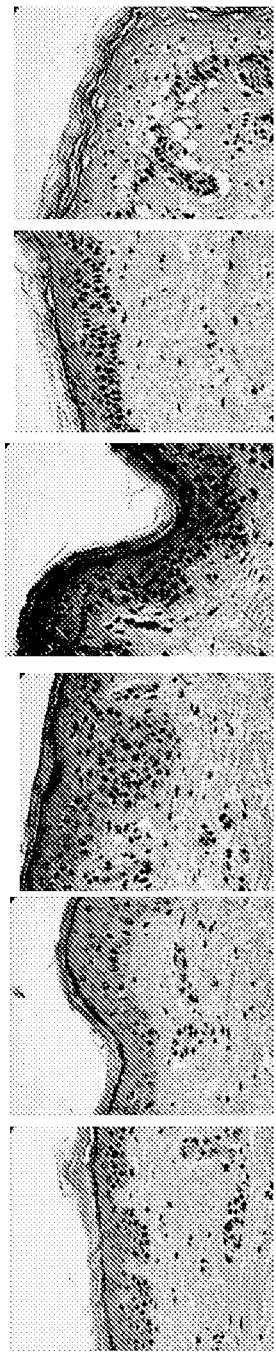
FIG. 7a comprises a series of photo micrographs of ex-vivo skin tissue cultured at 37 Celsius at 95% relative humidity over a time course of 11 days.
Figure 8:
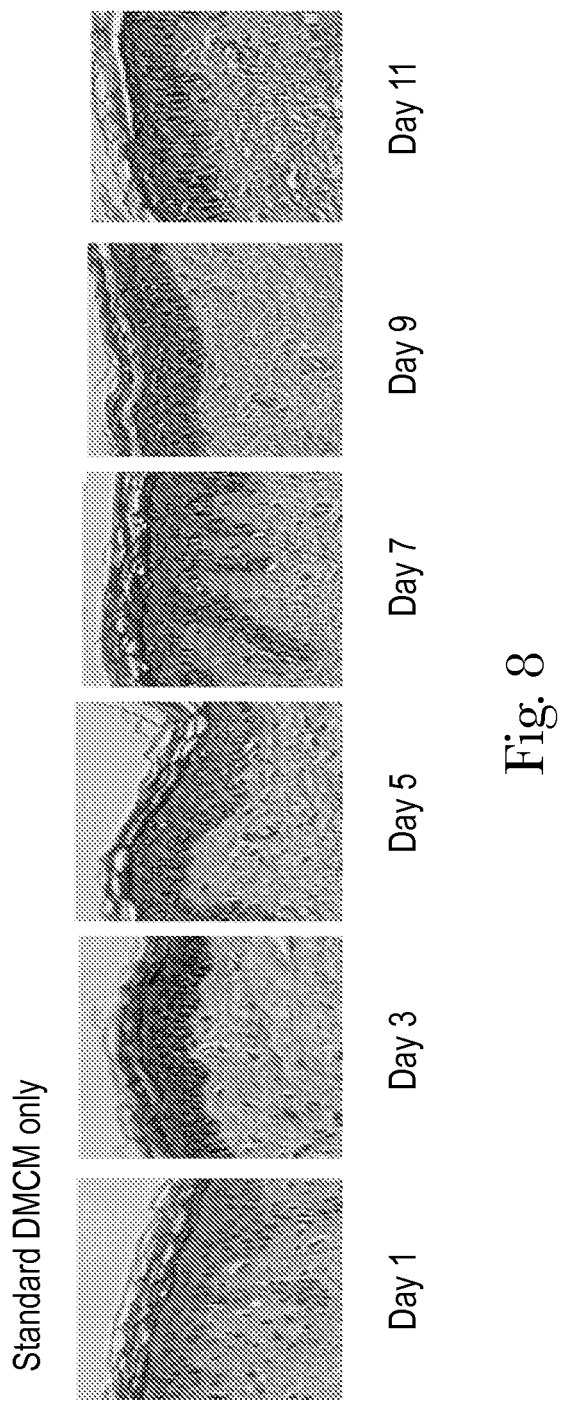
FIG. 8 shows a series of photo micrographs of ex-vivo skin tissue cultured at 33 Celsius at 70% relative humidity over a time course of 11 days.

Referring to FIG. 7a, ex-vivo skin tissue cultured at 37° C. and 95% humidity is shown from the date of arrival out to 11 days in minimal DMEM (minimal DMEM refers to DMEM with as few components added as possible to minimize additional variables). As can be seen, the tissue morphology degraded substantially over this time period. In comparison, FIG. 8 illustrates an ex-vivo tissue sample cultured at 70% humidity and 33° C. out to 11 days, wherein the morphology of the tissue remains largely intact over this time period.

Figure 7B:
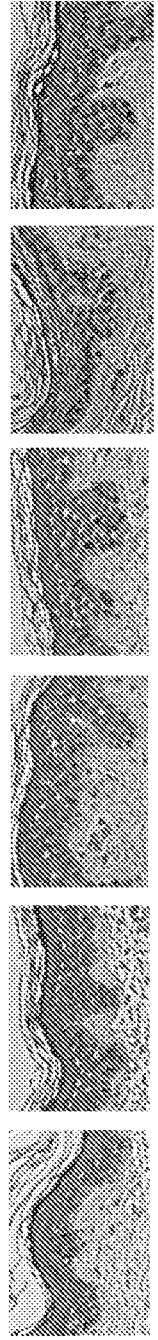
FIG. 7b comprises a series of photo micrographs of H&E stains of ex-vivo skin tissue cultured at 37 Celsius at 50% relative humidity over a time course of 10 days.
Figure 9:
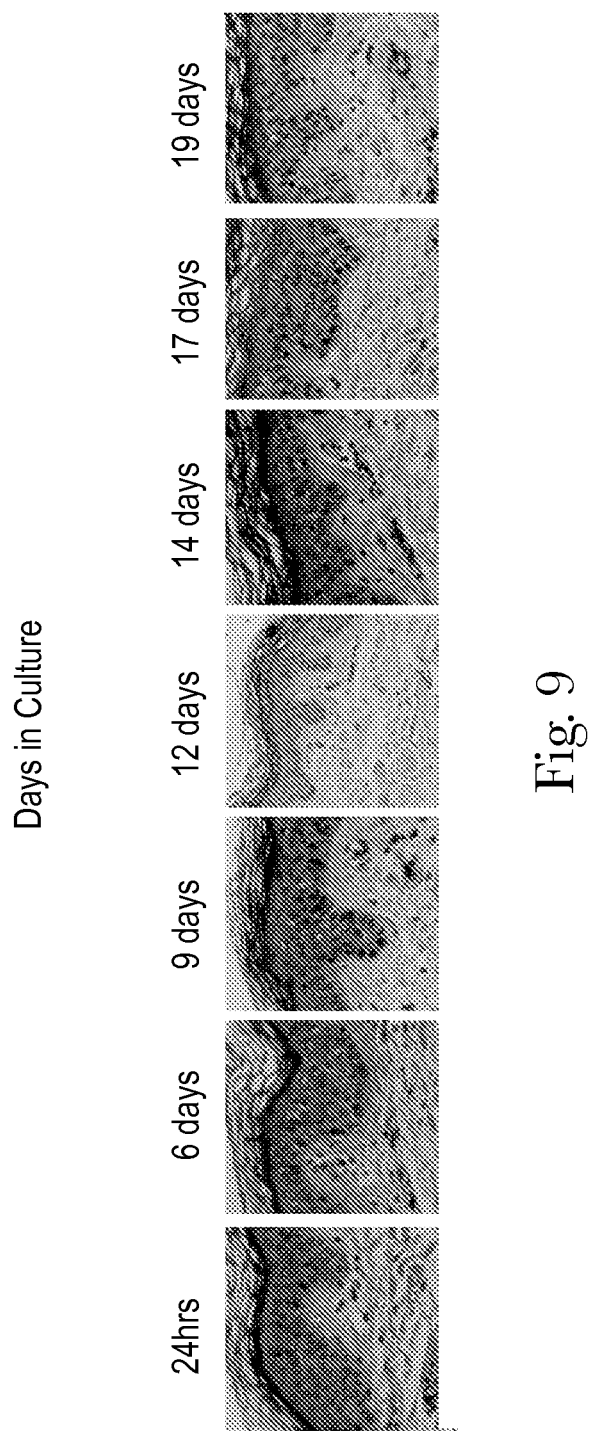
FIG. 9 shows a series of photo micrographs of ex-vivo skin tissue cultured at 33 Celsius at 70% relative humidity over a time course of 19 days.
Figures 11A, 11B:
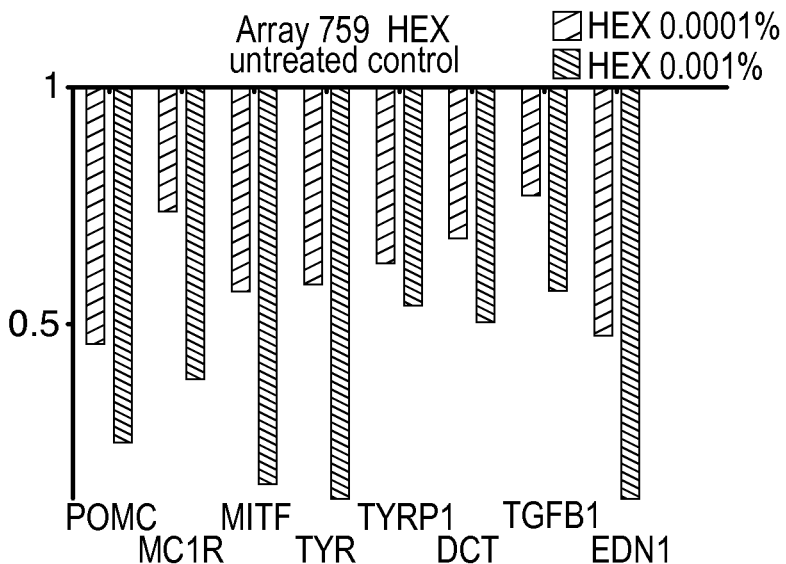
FIG. 11A is a bar graph showing the fold change versus an untreated control for certain tone genes of interest in an endogenously driven ex-vivo skin tissue following the treatment with 2 concentrations of hexamidine.
FIG. 11B is a table setting forth the fold regulation change for the data shown in FIG. 11A.
Figures 12A, 12B:
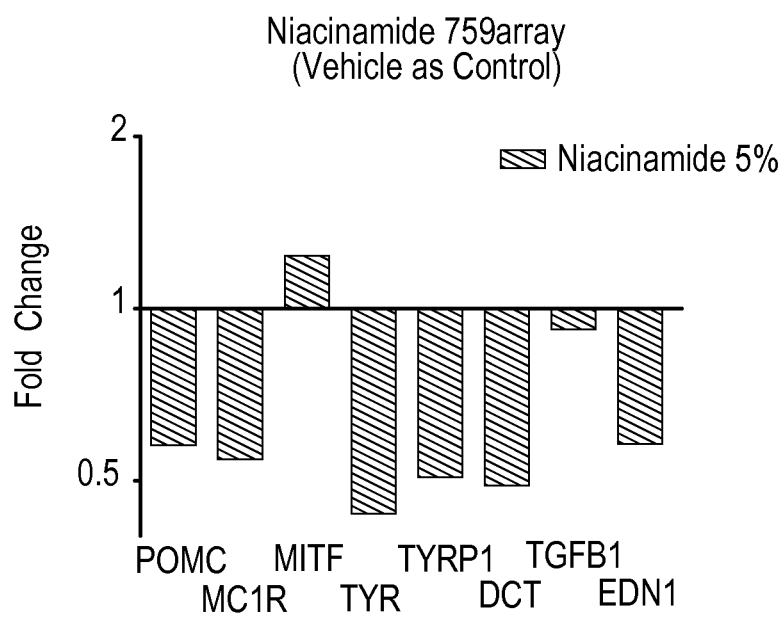
FIG. 12A is a bar graph showing the fold change versus an untreated control for certain tone genes of interest in endogenously driven ex-vivo skin tissue following treatment with niacinamide.
FIG. 12B is a table setting forth fold regulation for the data shown in FIG. 12A.
Figures 13A, 13B:
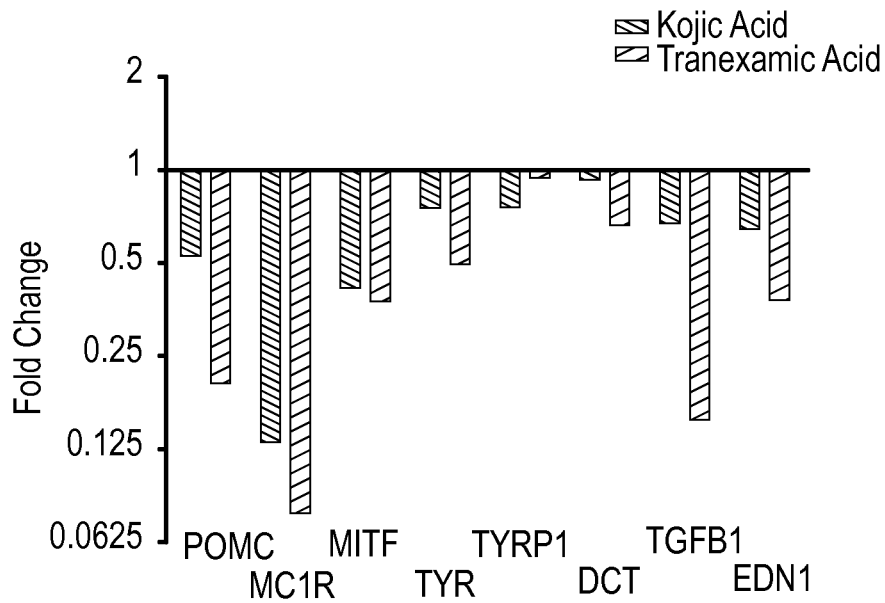
FIG. 13A is a bar graph showing the fold change versus an untreated control for certain tone genes of interest in endogenously driven ex-vivo skin tissue following treatment with kojic acid and tranexamic acid.
FIG. 13B is a table setting forth fold regulation for the data shown in FIG. 13A.
Figures 14A, 14B:
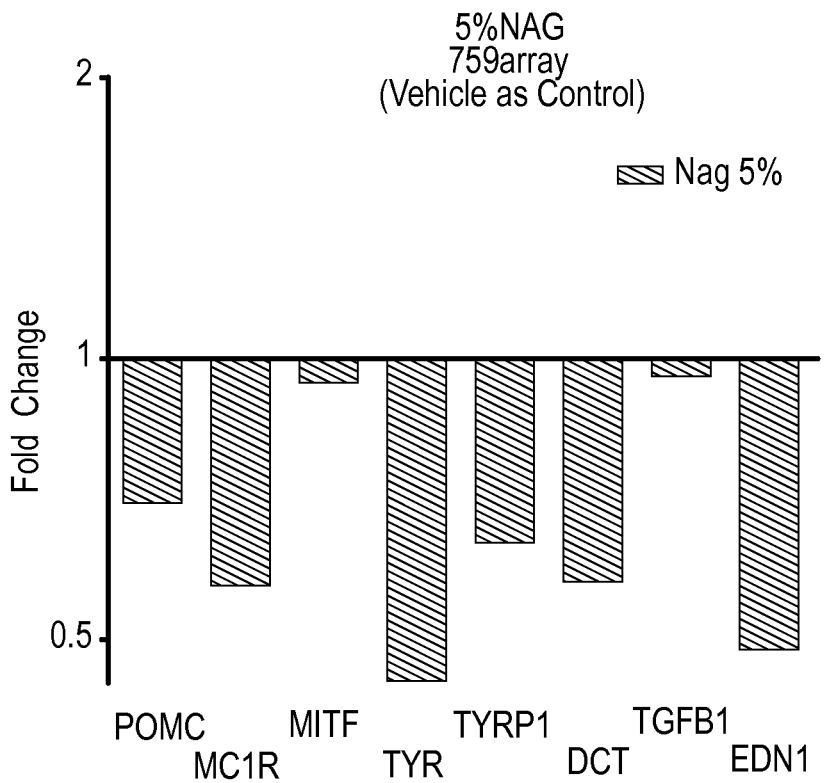
FIG. 14A is a bar graph showing the fold change versus an untreated control for certain tone genes of interest in endogenously driven ex-vivo skin tissue following treatment with 2 concentrations of N-acetyl glucosamine.
FIG. 14B is a table setting forth fold regulation for the data shown in FIG. 14A.
Figures 15A, 15B:
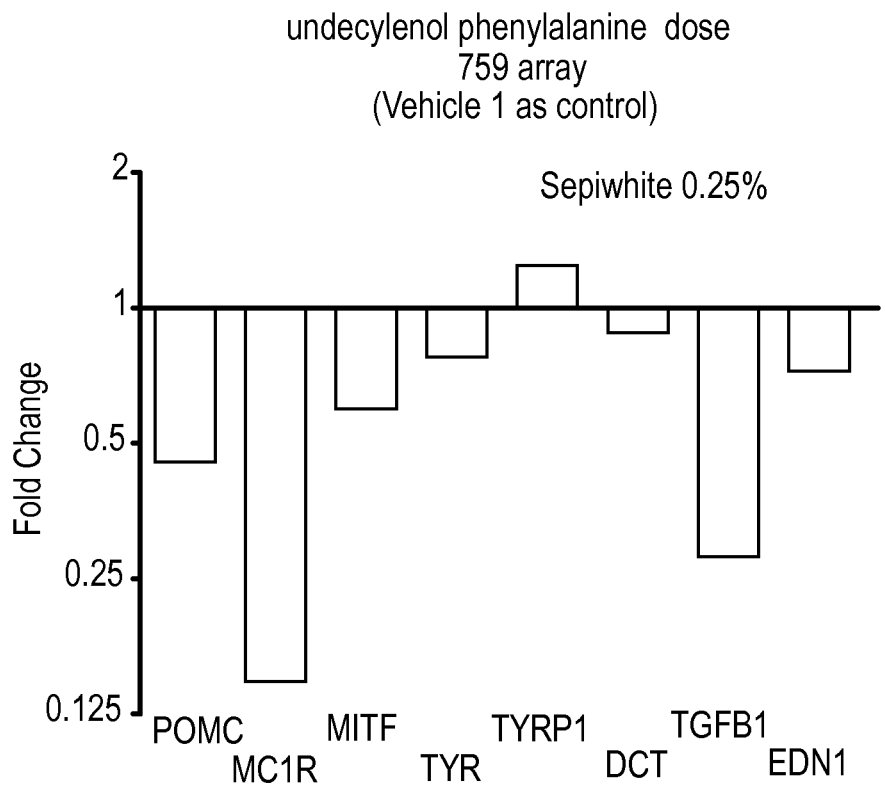
FIG. 15A is a bar graph showing the fold change versus an untreated control for certain tone genes of interest in endogenously driven ex-vivo skin tissue following treatment with 2 concentrations of undecylenoyl phenylalanine.
FIG. 15B is a table setting forth fold regulation for the data shown in FIG. 15A.

In specific embodiments the human skin tissue sample is cultured in an environment of less than 100% humidity. In various instances, the human skin tissue sample is cultured at a relative humidity from about 50% and about 90% or from about 50% to about 70% and/or in combination with a culturing temperature from about 30° C. and about 40° C. or from about 35° C. to about 40° C. In fact, the investigators have cultured ex-vivo skin tissue out to 19 days (at, for example, 70% humidity and 33° C.) while still maintaining tissue viability and/or morphology (see, e.g., FIG. 9). In another embodiment, the tissue samples can be cultured at about 50% relative humidity and about 37° C. (see, e.g., FIG. 7b). The cultures may or may not be sealed and may or may not have a cover or top that can affect internal humidity. The cultures also may be in specific embodiments, be cultured from 24 hours to 10 days.

While certain ranges for temperature, time and humidity have been provided herein, it will be appreciated that one or more of these described ranges can be increased or decreased. For example, temperature, humidity and culturing time can be affected by which positive control(s) is utilized. Tissue toxicity may limit the culturing time, which in turn may drive the selection of the temperature and humidity to provide the desired level of endogenous inflammation in the tissue sample.

Test Agents and Tissue Feeding

In specific embodiments, the ex-vivo skin tissue is contacted with at least one test agent of interest. The ex-vivo skin tissue may be dried prior to daily application of a topical formulation and/or wiping the sample to remove any non-absorbed formulation or chemical previously applied. In certain cases the hydration level of the sample can be tested one or multiple times and the sample can be dried one or multiple times or at each feeding to produce optimal results. The ex-vivo skin tissue may be feed based on cellular metabolic rates; feedings can be multiple times a day, every day, every other day, or on specific days throughout a multi-week period (such as 2, 3, or more). The feedings can be temperature dependent, such as daily feedings for cultures maintained at 37 degrees Celsius and every other day for cultures maintained at 33 degrees Celsius.

IV. Gene Transcriptomics and Positive Controls

When developing an ex-vivo skin assay, the investigators faced a choice whether to assay against a protein endpoint (e.g., Eumelanin) and/or mRNA endpoint. Protein levels can be variable and protein isolation is complicated by the amount of large, poorly soluble, matrix molecules in the skin sample. While an mRNA endpoint is attractive due to the higher analytical through-put rate provided by modern microarray technology, significant challenges and uncertainties are associated with measuring this endpoint, including but not limited to whether ex-vivo skin could be properly regulated at the transcriptomic level for a sufficient period of time, whether appropriate positive controls could be identified that provided consistent and proper regulation of the tone genes of interest over a sufficient percentage of the donor population, whether a transcriptomic analysis could be predictive of in vivo results, and whether adequate RNA could be obtained for analysis and maintained considering multiple possible sources for introduction of RNases that could degrade the RNA. The positive controls ideally, although not necessarily, should be selected to generally provide the same effect/directionality of gene regulation (typically down regulation) as a potential test agent of interest. The ability of known tone benchmark agents to fulfill this role as positive controls was an added uncertainty.

In addition, a confounding factor faced by the investigators related to the dual-relationship of genes regulating tone potentially also being stress-related genes (or interacting with stress-related genes), since ex-vivo skin tissue is in an inherently stressed state. Utilizing agents to increase or decrease genes in a controlled manner is complicated by dosing, time, and inherent gene states that can be complicated by genetic stressor responses that can also have an effect on or be regulated by tone genes. Such dual-relationships of genes regulating tone and stress responses could have easily muddled result analysis and complicated data results and interpretations. A further uncertainty was whether benchmarks (even potential benchmarks showing clinical promise) would work consistently enough at a genetic level to be used as positive controls across a large donor population (e.g., at least about 40%, 50%, 60%, 70% or even 80% of the tissue samples). The positive controls are used to assess whether tone genes of interest in the donor tissue are properly regulated under the test conditions (e.g., the genes of interest or up or down regulated as would be expected for the tissue state) and to assist with interpretation of the transcriptomic data related to the test compound. Thus, by selecting and utilizing known benchmark tone compounds as positive controls, the gene expression could be determined for an array of genes related to skin pigmentation and a statistically significant transcriptomic pattern could hopefully be obtained that was consistent across a relevant portion of the donor population. This pattern could be then be used to confirm proper regulation of the donor tissue during a test and to analyze the effect upon the same genes by the application of new agents to affect skin pigmentation and predict clinical success by gene regulation patterns. In this way, donor to donor variability relating to the genomic state of the tissue sample could also be addressed in the screening method.

The investigators identified approximately 15 dermal and epidermal genes as possible candidates for mRNA endpoint analysis along with several "housekeeping" genes. These genes are listed in FIG. 10. The dermal and epidermal genes involved in the pigmentation process as described in the literature were reviewed and a list of candidates genes offering promise for testing was selected. Housekeeping genes were chosen as genes that were expected to remain unchanged given provided treatments; to ensure this, multiple housekeeping genes were chosen. Samples were of approximately the same size, and to ensure consideration of approximately equal cell numbers per sample, results were normalized to housekeeping genes. The epidermal genes include, but are not limited to, Propriomelanocortin, Melanocortin 1 Receptor, Microphthalmia-associated transcription factor, Tyrosinase, Tyrosinase Related Protein 1, Docrachrome Tautomerase, Transforming Growth Factor-Beta 1, and Endothelin 1. While these genes are discussed hereafter for purposes of simplicity, it will be understood that this is a non-limiting selection of genes suitable for use with the methods herein and that other genes may be added or substituted and that not all the genes set forth in FIG. 10 need be incorporated in the methods described herein.

From this list, the investigators have found that the epidermal genes are generally more consistently regulated by potential positive controls (e.g., benchmark tone compounds such as niacinamide, hexamidine, N-Acetyl glucosamine, kojic acid, and tranexamic acid, and undecylenoyl phenylalanine) than the dermal genes, although there was a fair amount of variability even among the epidermal genes. Referring to FIGS. 11 to 15, examples are shown for the regulation of the 9 epidermal tone genes against an untreated control in an endogenously driven ex-vivo tissue system at 37° C. and 70% humidity for niacinamide, hexamidine, N-Acetyl glucosamine, kojic acid, tranexamic acid, and undecylenoyl phenylalanine (2-10 experiments each). The data suggests that there is certain variability amongst the benchmark compounds. For instance, out of the 9 epidermal genes, at least one compound (Hexamidine) regulated 9 genes (with a statistical significance of $p<0.1$ or better) while two compounds regulated 5 or fewer genes (with a $p<0.1$ or better). Table 1 below summarizes the number of epidermal genes regulated by certain materials in an endogenously driven tissue sample with a statistical significance of $p \leq 0.1$.

TABLE 1

| Technology | # Genes (out of 9) with $p \leq 0.1$ |
|---|---|
| Hexamidine | 9 |
| Niacinamide | 7 |
| Tranexamic | 7 |
| NAG | 6 |
| Kojic Acid | 5 |
| Undecylenoyl phenylalanine | 3 |

In specific embodiments of the screening methods, the transcriptional profile consists of data related to transcription of at least two genes selected from the group Propriomelanocortin, Melanocortin 1 Receptor, Microphthalmia-associated transcription factor, Tyrosinase, Tyrosinase Related Protein 1, Dochrachrome Tautomerase, Transforming Growth Factor 1, and Endothelin 1. In other embodiments the transcriptional profile consists of data related to transcription of Propriomelanocortin, Melanocortin 1 Receptor, Microphthalmia-associated transcription factor, Tyrosinase, Tyrosinase Related Protein 1, Dochrachrome Tautomerase, Transforming Growth Factor 1, and Endothelin 1.

In specific embodiments, the ex-vivo screening methods utilize 1, 2, 3, 4 or more positive controls that regulate 2, 3, 4, 5, 6, 7, 8, 9 or more genes of interest (which in specific embodiments include 2 to 9 genes from FIG. 10) with a p≤about 0.1 or a p≤about 0.05. Depending on penetration characteristics of the positive control, an agent or agents can be added to either the media or applied topically (including as a non-limiting example, applied topically to the epidermis). For example, hexamidine may be added to the media due to its low penetration topically.

In specific embodiments, a second human skin tissue sample is screened with a benchmark tone agent as a positive control (and a human donor tissue sample can be in specific cases divided into at least a first and second human tissue sample). The benchmark tone agent may, in specific embodiments, be niacinamide, hexamidine, undeclenoyl phenylalanine, N-acetyl glucosamine, kojic acid, tranexamic acid, and combinations thereof. The screening process for a second human skin tissue sample can additionally comprise generating a transcriptional profile related to two or more genes from FIG. 10, and may comprise use of a benchmark tone agent wherein the benchmark tone agent up regulates or downregulates genes (such as two or more genes from FIG. 10) either up or down for skin tone benefit. A skin tone benefit may be any change in skin tone and/or skin pigmentation overall or locally (e.g., as in an age sport or Senile Lentigo).

In specific embodiments, an analysis of mRNA regulation related to genes selected from FIG. 10 involves a review of genes that directly lead to a change in melanin levels, such as tyrosinase (TYR), tyrosinase-related protein-1 (TYRP1) or dopachrome tautomerase (TYRP1 or DCT), and the analysis can be separate from or in combination with an analysis of genes that can indirectly affect melanin levels (such as transcription factor microphthalmia-associated transcription factor (MITF)). The analysis of one or more mRNA levels in specific embodiments can include a statistical analysis (in specific embodiments including p values) or fold changes or fold regulation for statistically significant changes, trends, or patterns observable visually (through graphic representation or as presented from mRNA levels in tables). In other specific embodiments, an experiment may be repeated if a human skin tissue sample does not show a response to treatments, in which case a second experiment may be performed to ensure experimental results are not due to a false negative.

Screened test samples can, in specific instances, be from surgical waste tissue, be cultured on a membrane, or either include a subcutaneous fat layer or include a sample that has had the subcutaneous fat layer removed (and in the specific embodiments where a human donor tissue sample is divided into at least a first and second human donor tissue sample, the subcutaneous fat layer can be removed before the dividing). Screening in certain embodiments involves repeating the screening with tissue from the same or different donors for a plurality of test agents. Screening can also involve applying an energy source to tissue to mimic a skin tissue phenotype, can involve a skin tissue phenotype that is an age spot or photo response, and/or can additionally involve topical application of a paracrine agent (e.g., in certain instances is stem cell factor and/or endothelin-1, from 40 ng/ml to 100 ng/ml each). Screening can also involve formulating a cosmetic skin care composition comprising the test agent. Screening can also involve an adult human skin tissue sample wherein the sample has a dermis and an epidermis side and where the dermis side is placed dermis side down in an isosmotic solution to keep the dermis moist and the epidermis dry.

The investigators identified positive controls that can provide a 50 to 75 percent success rate such that the screening method could be utilized when testing hundreds to thousands of ex-vivo tissue samples. This level of success is useful due to the fact that use of an organ system for compound screening over hundreds of screens requires a level of consistency previously unseen and well beyond that of primary academic research studies which typically require minimal sample sizes for statistical comparisons.

IV. Compound and Energy Driven Screening Methods

While an endogenously driven screening method has certain benefits over a compound driven screening method with respect to selection of benchmarks and transcriptomic consistency, in specific embodiments a compound or energy (e.g., an electromagnetic energy or optical source) driven screening method may be desirable. In a compound driven screening method, one or more compounds may be topically applied or added to the tissue culture media to increase the up-regulation of one or more of the tone genes of interest beyond that provided by endogenous tissue inflammation or to mimic a tissue phenotype, such as an age spot. In an energy driven screening method, a source of electromagnetic energy, such as ultraviolet light, may be administered to the tissue sample to increase the up-regulation of one or more of the tone genes of interest beyond that provided by endogenous tissue inflammation or to mimic a tissue phenotype.

Compound-Driven Ex-Vivo Skin Tissue Methods

A variety of agents that increase tissue inflammation may be utilized, including but not limited to: Interleukin 1 Alpha, Interleukin 1 Beta, Tumor Necrosis Factor Alpha, Interleukin 17, Forskolin, MSH, Endothelin 1, Stem Cell Factor, and combinations thereof. In specific embodiments, Interleukin 17 or Interleukin 1 or Tumor Necrosis Factor Alpha may be applied to a skin tissue sample to increase inflammation. In other embodiments, paracrine agents or one or more cytokines may be utilized to up regulate genes to drive various types of inflammation. Any stressors utilized can be applied in various embodiments within 24 hours of the start of culture.

Figures 16A, 16B:
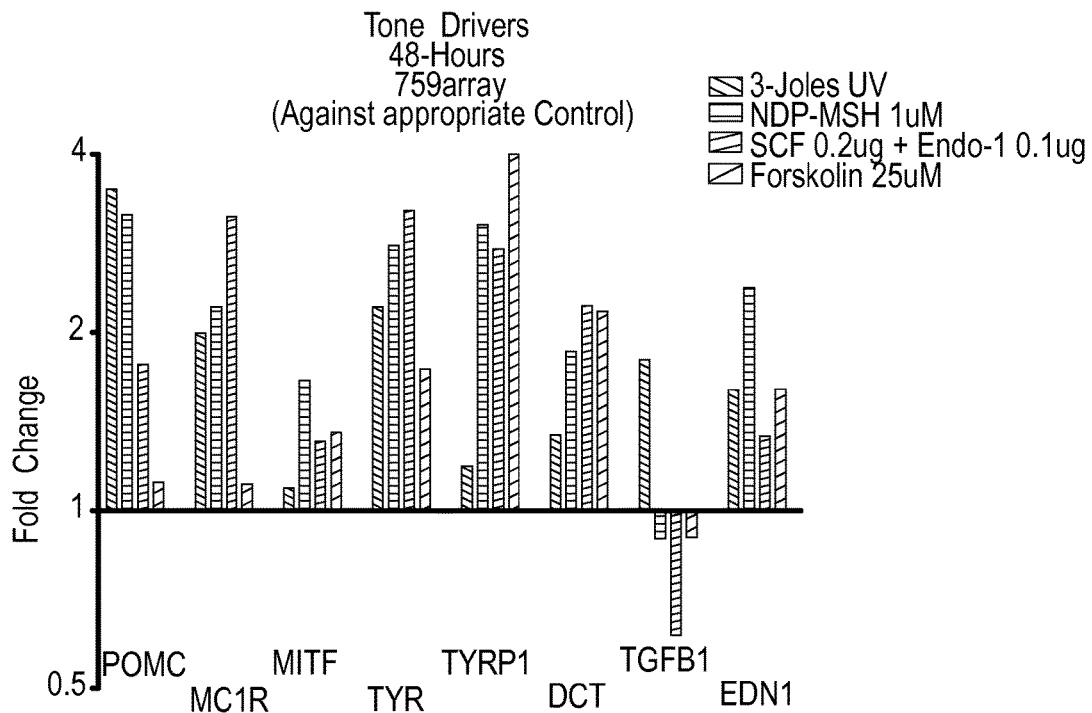
FIG. 16A is a bar graph illustrating the fold change for certain tone genes of interest in ex-vivo skin tissue following exposure to various compounds know to up-regulate the pigmentation pathway.
FIG. 16B is a table setting forth fold regulation for the data shown in FIG. 16A.

Referring to FIG. 16, it can be seen that a variety of compounds known to stimulate the pigmentation pathway (e.g., Forskolin, Stem Cell Factor, and α-MSH) can likewise up regulate one or more tone genes of interest, with a p≤0.1 in an ex-vivo tissue culture (results include a minimum of 2-10 experiments each). This not only demonstrates that tone genes of interest can be properly regulated in an ex-vivo tissue culture consistently across at least a portion of a donor population sufficient to make a commercial screening method viable (where perhaps hundreds or thousands of different donors are used) but this up-regulation of certain genes may also be used to mimic certain tissue phenotypes, such as for example age spots.

It has been suggested that Stem Cell Factor is implicated in the formation of age spots (see Hattori et al. The Epidermal Stem Cell Factor is Over-Expressed in Lentigo Senilis: Implication for the Mechanism of Hyperpigmentation, The Journal of Investigative Dermatology, May 5 of 2004, pp 1256-65). It has also been suggested that Endothelin is implicated in the formation of age spots (Imokawa et al., Endothelin-1 as a New Melanogen: Coordinated Expression of Its Gene and the Tyrosinase Gene in UVB-Exposed Human Epidermis, Journal of Investigative Dermatology (1995), 105, pp 32-37).

Figure 17:
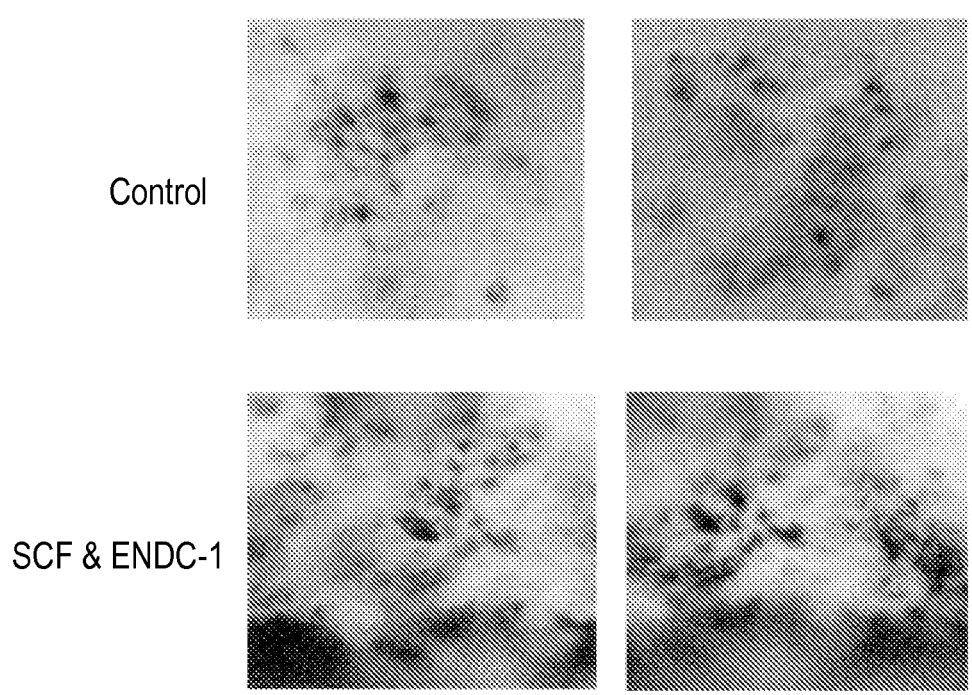
FIG. 17 shows epidermal tissues stains from ex-vivo tissue exposed to a combination of Stem Cell Factor and Endothelin 1 versus an untreated control.
Figure 18:
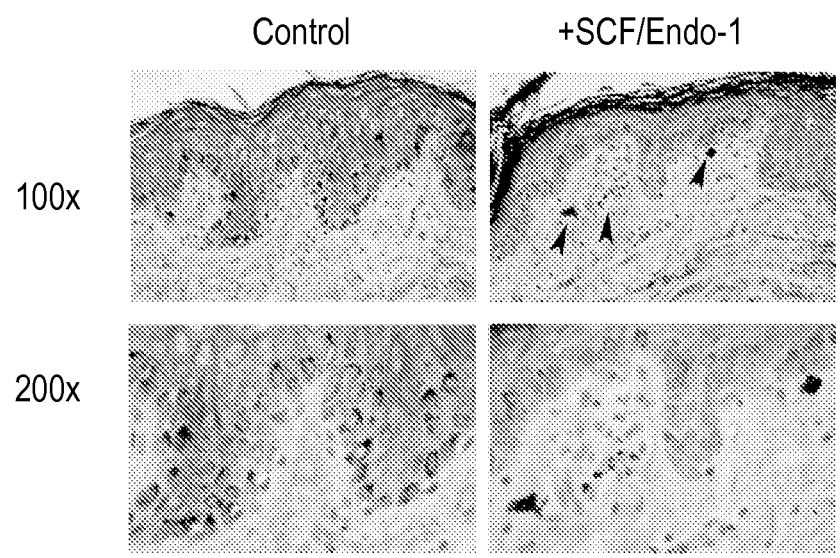
FIG. 18 shows photomicrographs from ex-vivo tissue exposed to a combination of Stem Cell Factor and Endothelin 1, wherein arrows illustrate structures believed to be melanophages.
Figures 19A, 19B:
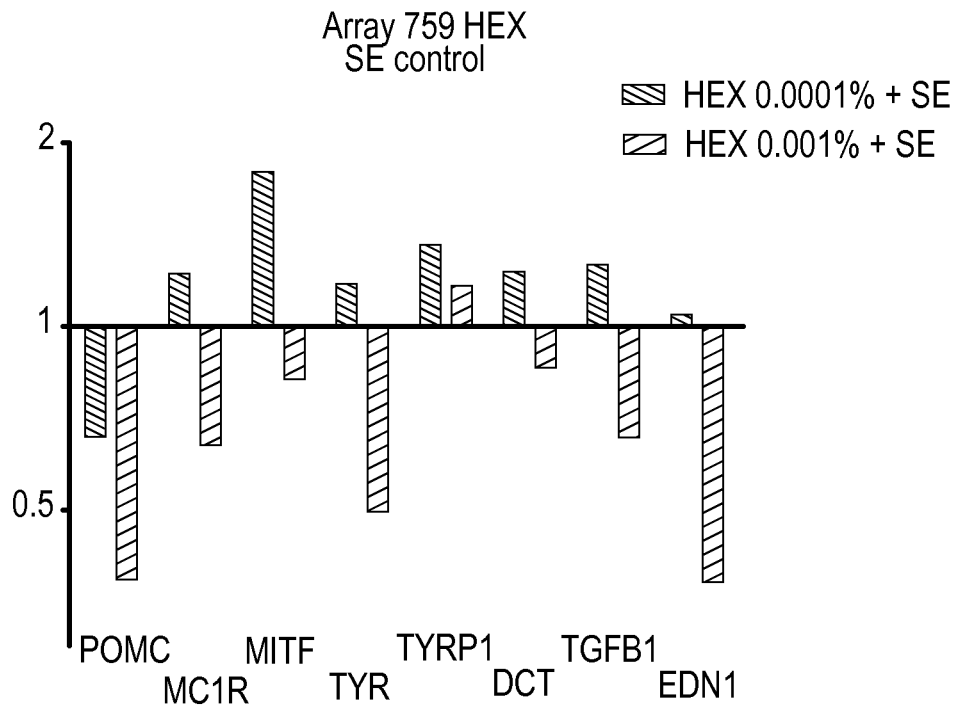
FIG. 19A is a bar graph showing the fold change versus an untreated control for certain tone genes of interest in an endogenously driven ex-vivo skin tissue following the treatment with 2 concentrations of hexamidine.
FIG. 19B is a table setting forth the fold regulation change for the data shown in FIG. 19A.
Figures 20A, 20B:
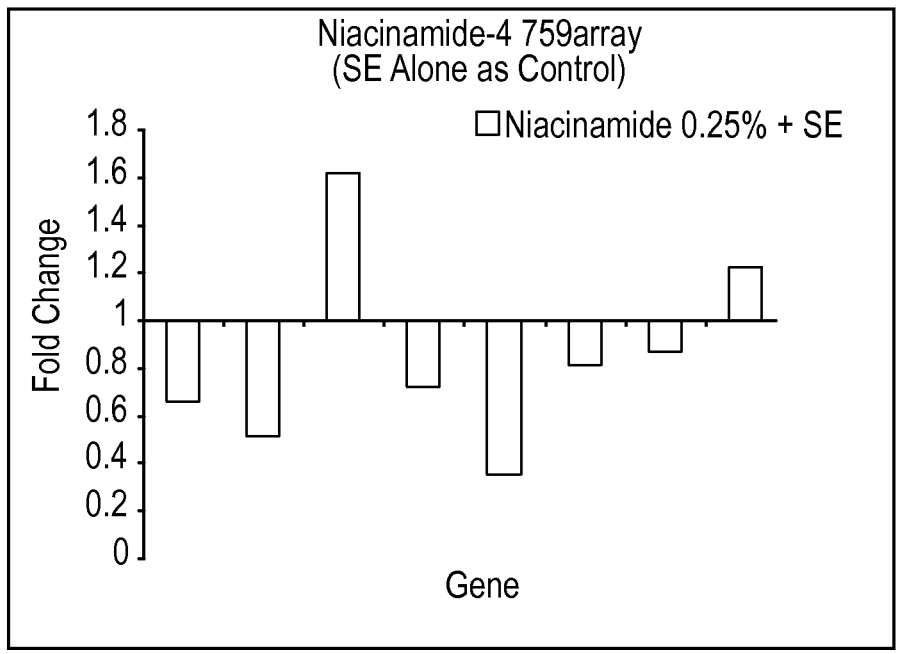
FIG. 20A is a bar graph showing the fold change versus an untreated control for certain tone genes of interest in ex-vivo skin tissue (driven by a combination of Stem Cell Factor and Endothelin 1) following treatment with niacinamide.
FIG. 20B is a table setting forth the fold regulation change for the data shown in FIG. 20A.
Figures 21A, 21B:
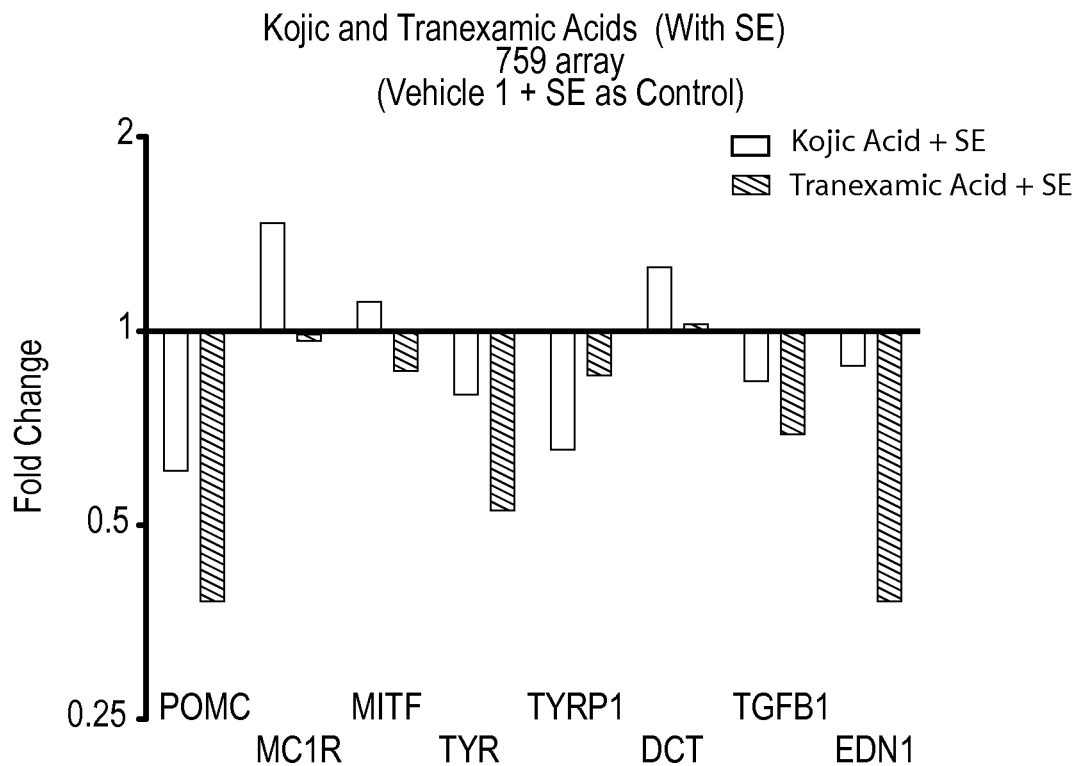
FIG. 21A is a bar graph showing the fold change versus an untreated control for certain tone genes of interest in ex-vivo skin tissue (driven by a combination of Stem Cell Factor and Endothelin 1) following treatment with kojic acid and tranexamic acid.
FIG. 21B is a table setting forth the fold regulation change for the data shown in FIG. 21A.
Figures 22A, 22B:
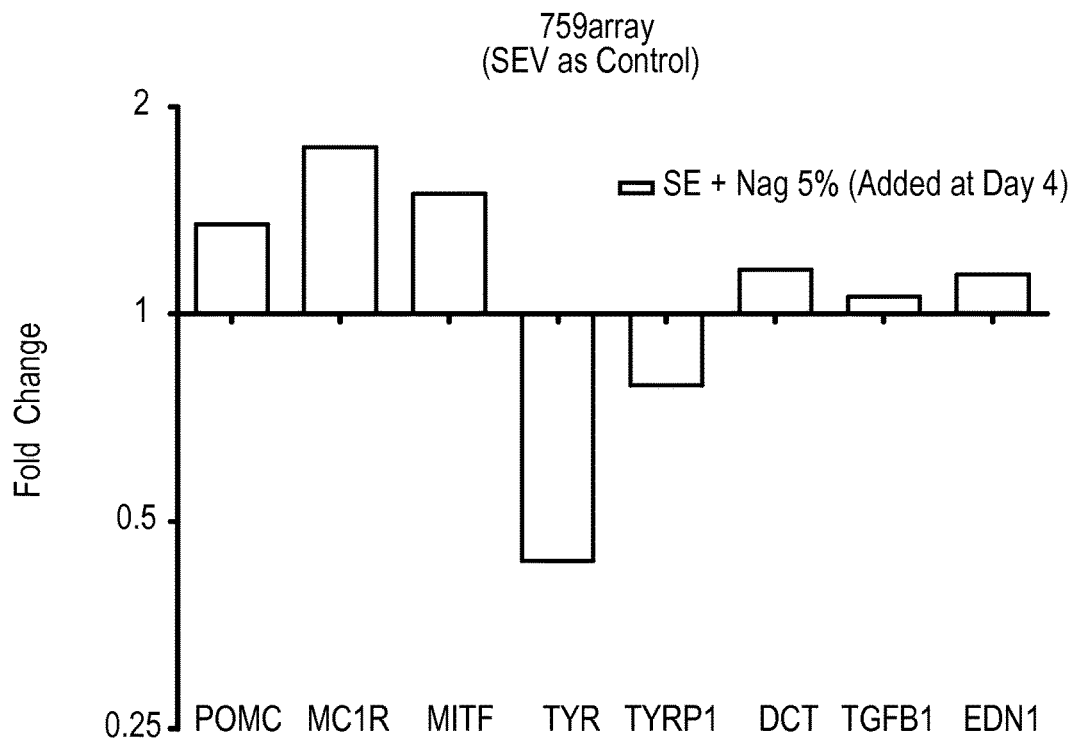
FIG. 22A is a bar graph showing the fold change versus an untreated control for certain tone genes of interest in ex-vivo skin tissue (driven by a combination of Stem Cell Factor and Endothelin 1) following treatment with 2 concentrations of N-acetyl glucosamine.
FIG. 22B is a table setting forth the fold regulation change for the data shown in FIG. 22A.
Figure 23A:
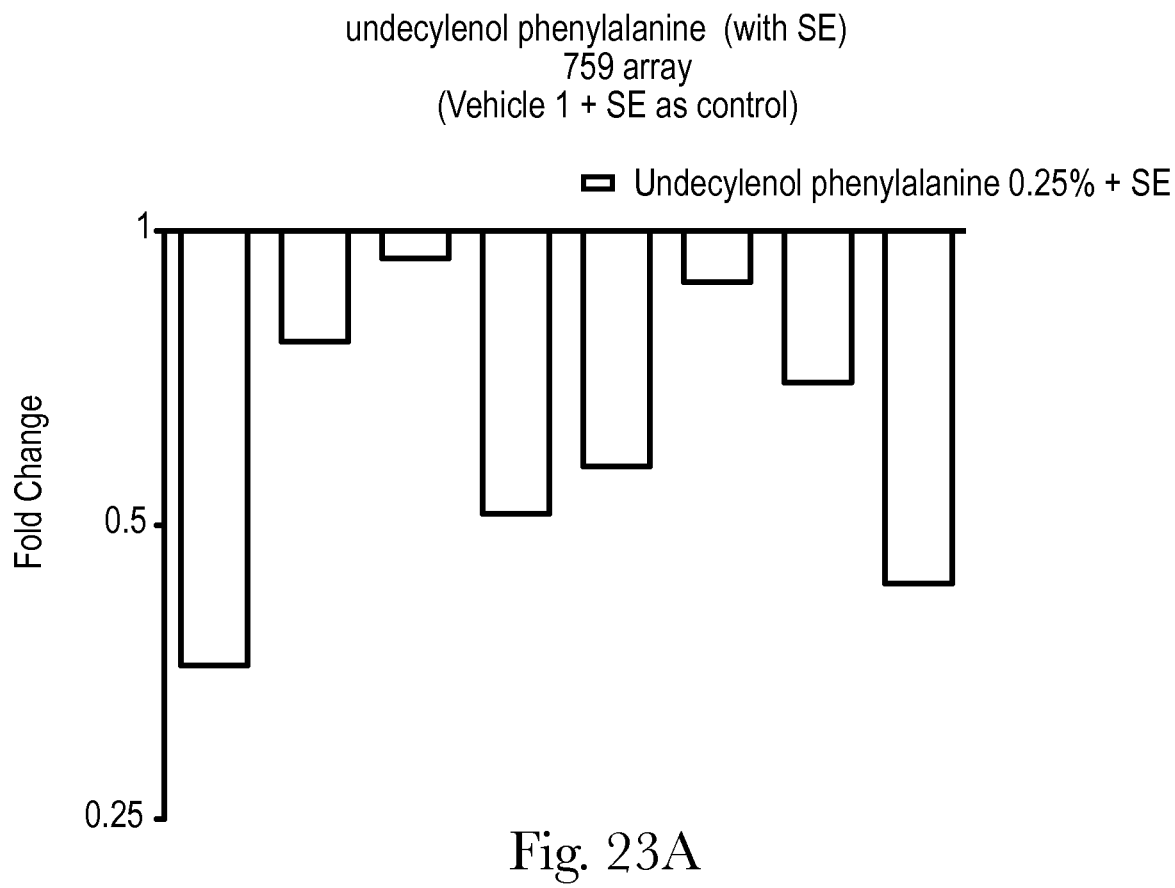
FIG. 23A is a bar graph showing the fold change versus an untreated control for certain tone genes of interest in ex-vivo skin tissue (driven by a combination of Stem Cell Factor and Endothelin 1) following treatment with 2 concentrations of undecylenoyl phenylalanine.
Figure 23B:
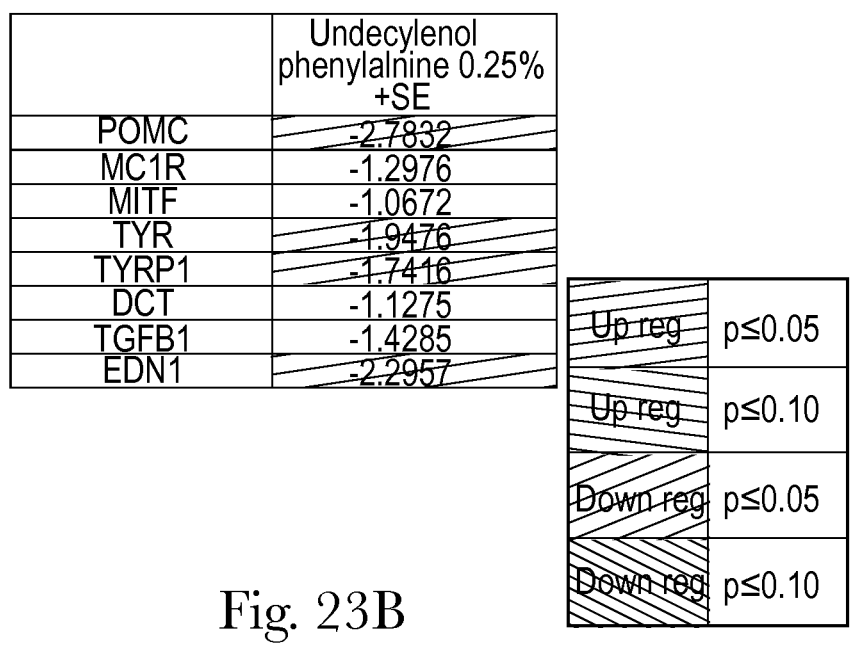
FIG. 23B is a table setting forth the fold regulation change for the data shown in FIG. 23A.

Application of Stem Cell Factor in combination with Endothelin 1 to an ex-vivo tissue culture surprisingly yielded histology results that appear to mimic an age spot phenotype. Referring to FIG. 17, Fontana-Masson staining of epidermal preparations of the ex-vivo tissue culture show increased pigmentation versus a control after exposure to a combination of Stem Cell Factor/Endothelin 1. Thus, it appears that it may be possible to duplicate certain tissue phenotypes related to tone in ex-vivo tissue samples. In specific embodiments of the screening methods, the ex-vivo human skin tissue sample is exposed to at least one of Endothelin 1 or Stem Cell Factor; the concentration of Endothelin 1 can be between about 40 ng/ml and about 80 ng/ml and the concentration of Stem Cell Factor can be between about 40 ng/ml and about 80 ng/ml.

While compounds or materials may be added either topically or to the culture media to up-regulate the tone genes of interest in the ex-vivo tissue sample, the investigators have found that it can be more challenging to consistently detect down-regulation of these genes by a test agent or positive control in certain instances. Referring to FIGS. 19 to 23, examples (of 2-10 experiments each) are shown for the regulation of the 9 epidermal tone genes against an untreated control in ex-vivo tissue driven by the combination of Stem Cell Factor and Endothelin at 37° C. and 70% humidity for niacinamide, hexamidine, N-Acetyl glucosamine, kojic acid, tranexamic acid, and undecylenoyl phenylalanine. The data suggests that there is more variability amongst the benchmark compounds than for the endogenously driven system (see, e.g., FIGS. 11 to 15). For instance, out of the 9 epidermal genes, at least one compound (undecylenoyl phenylalanine) regulated 5 genes (with a statistical significance of p<0.1 or better) while two compounds regulated 2 or fewer genes (with a p<0.1 or better). Table 2 below summarizes the number of epidermal genes regulated by certain materials in a Stem Cell Factor/Endothelin 1 driven tissue sample with a statistical significance of p≤0.1.

TABLE 2

| Technology | # of Genes with p ≤ 0.1 |
|---|---|
| Undecylenoyl phenylalanine | 5 |
| Hexamidine | 4 |
| Niacinamide | 3 |
| Tranexamic | 3 |
| Kojic Acid | 2 |
| NAG | 1 |

There can be advantages to utilizing a compound driven screening method with ex-vivo skin tissue; however it appears such screening methods may not provide the same level of consistent and detectable regulation of the tone genes of interest by positive controls and/or test compounds (both being down regulating compounds) as in an endogenously driven screening method.

Energy Driven Ex-Vivo Skin Tissue Methods

In specific embodiments, it may be desirable to subject the ex-vivo tissue sample to an electromagnetic radiation source, such as, for example, to induce a photo response or tanning phenotype that may be used in a screening method. The ultraviolet light may be used to up regulate one or more tone genes of interest of the human skin tissue sample, after which a gene transcriptional analysis may be conducted to assess gene expression changes relative to an untreated control. In specific embodiments, the tissue sample may be subjected to from about 50 mJ to about 10 J of energy for a period of time from about 2 hours to about 48 hours or from about 2 hrs to about 24 hrs, wherein energy is in the ultraviolet spectrum (e.g., from about 10 nm to about 400 nm). In other embodiments, the tissue sample may be subjected to from about 2 J to about 10 J of energy for a period of time from about 2 hours to about 48 hrs. Gene transcriptional analysis may conducted between 2 hrs and about 96 hrs or more after exposure to the electromagnetic radiation source.

Figure 24:
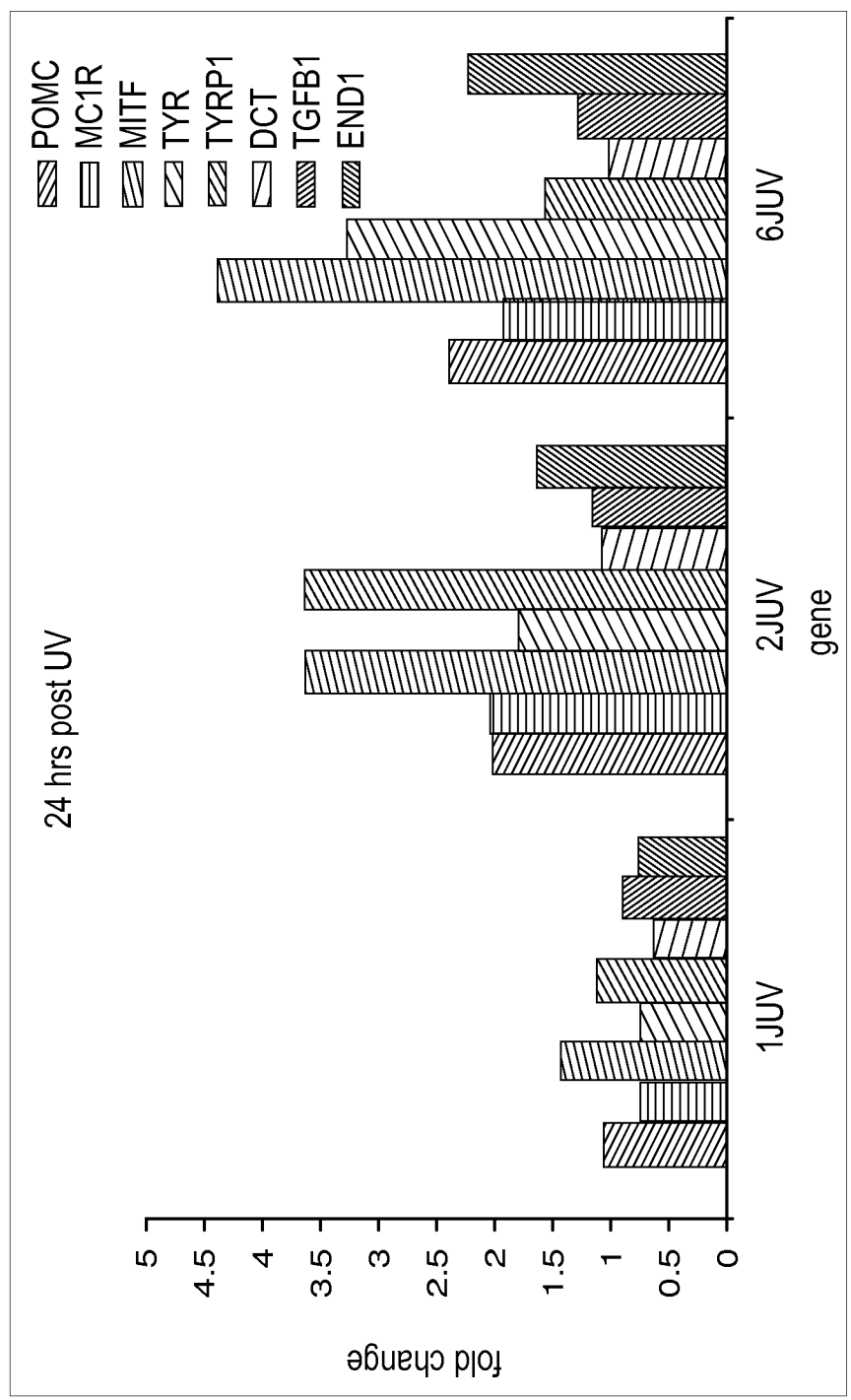
FIG. 24 is a bar graph showing the fold change of certain tone genes of interest versus an untreated control following exposure to ultraviolet radiation.

Referring to FIG. 24, it can be seen that a 2 J and 6 J treatment up-regulated various tone genes of interest, as measured 24 hrs after the UV exposure as compared to a control not subjected to the UV energy. Particularly, FIG. 28 shows induction of propriomelancortin (POMC), Melanocortin 1 receptor (MC1R), Microphthalmia-associated transcription factor (MITF), Tyrosinase (TYR), Tyrosine related protein 1 (TYRP1), Dochrachrome tautaomerase (DCT), Transforming growth factor 1 (TGFB1), and Endothelin 1 (END1); FIG. 1B shows Fibroblast growth factor (FGF), v-KIT (KIT—the receptor for Stem Cell Factor (SCF)), Endothelin Receptor B (EDNRB), Hepatocyte Growth Factor (HGF), B-cell CLL/Lymphoma 2 (BCL2), BCL-2 associated protein (BAX), Lymphoid enhancer binding 1 factor (LEF1).

Ex-vivo skin tissue may be manipulated by either compounds or radiation sources to induce skin tone phenotypes. Induction of one or more of these phenotypes in ex-vivo skin tissue may then be used to screen for test compounds that mitigate, reduce, reverse, or ameliorate these phenotypes or otherwise down-regulate one or more tone genes of interest that are up-regulated in the driven skin tissue.

VI. mRNA Processing

The investigators also have provided surprising breakthroughs by accounting for variables that proved less indispensable for the screening method but nonetheless provided advantages and proved consequential for the screening method advancement (such as accounting for variables in tissue harvesting, transport, and tissue collection for data analysis, among others).

The method and model herein described may include human skin tissue samples that are pulverized or homogenized for analysis or additional analysis of material (to obtain DNA, RNA, or other materials or to analyze these materials).

The methods and models described herein can involve analysis of RNA from full or partial human skin tissue samples or from simple cell types removed from such samples (such as through laser microdis section or physical cell or cell layer removal or other ways known in the art). Dermal and epidermal layers may be removed and analyzed separately or together. Profiles can be generated from such individual cells, layers, or from multiple cells, layers, parts (or in whole) of the human skin tissue sample or samples.

Analysis of mRNA regulation following testing of an agent relating to a panel of genes known to regulate tone can provide the basis for identifying agents as effective for providing skin tone benefits. For example, in a non-limiting example, a pigmentation gene panel can be determined involving genes known to regulate tone, with the panel involving analysis of mRNA for genes such as POMC, MCR1, MITF, TYR, TYRP1, DCT, TGFB1, and EDN1.

In various non-limiting examples, identifying agents as effective for providing skin tone benefits can involve this panel of genes, and look at the directionally appropriate increase or decrease of the expression levels in comparison to an untreated control; a determination of an agent as being effective may involve two of the genes (being increased or decreased). In other examples, 5 genes of the panel, or all 8 have expression levels altered in response to the agent applied. In others, the panel consists of 10 genes, with various numbers of genes (such as 2, 3, 5, 8, 10) being related to a determination of effectiveness. A determination that an agent is effective can also involve statistical tests and/or statistical significance of replicate wells or tests. For example, replicates could involve a sample size (n) of 3 or 5 or 10 or more. Additionally, statistical significance of mRNA levels can be set at less than or equal to 0.05, 0.01, 0.01, 0.001, or can be set at alternate levels.

VII. Tiered Screening

In certain embodiments the screening method is used in repetition. The screening method can involve repeating the steps of providing, contacting, generating, comparing, and identifying, wherein the human skin tissue sample for each repetition is from a different donor. Each repetition may also involve a different test agent. A plurality of test agents may be screened. In some embodiments, greater than about 5, 10, 25, 50, 100, 200, 400, 800 and/or less than about 1000 or 800 test agents may be screened.

The screening methods described herein may also be combined with other screening methods to provide a tiered screening process. Tiers are associated with increased complexity per level; due to the fact each tier provides additional data, conclusions can be drawn to more accurately focus on promising agents. Therefore higher tiers are associated with a lower number of possible agents that have a higher probability of being effective.

Tiers may advance as follows: enzyme assays, cell-based cultures, in vitro assays, and ex-vivo skin assays of the present invention. Enzyme assays involve an analysis of protein functions, cell-based cultures involve simply cell cultures primarily in culture plates, and in vitro assays involve more complex culturing conditions with combined cell-types. Initial tiers can be completed relatively more quickly with higher outputs, while advanced tiers involve additional time and involve lower thru-put. An in-depth analysis of each tier provides end data allowing increased probabilities of success for tone-related agents.

VIII. Cosmetic Compositions

Because of the desirability of providing various cosmetic skin tone benefits to a consumer, it may be beneficial to incorporate test agents or compounds identified by one or more of the screening methods described herein into a cosmetic composition suitable for topical application to skin. That is, it may be desirable to include the test agent as an ingredient in the cosmetic composition. In certain embodiments, the cosmetic composition may include a dermatological acceptable carrier, the test agent, and one or more optional ingredients of the kind commonly included in the particular cosmetic compositing being provided. Non-limiting examples of such optional ingredients include vitamins; peptides and peptide derivatives; and sugar amines. Other optional ingredients include sunscreen actives (or sunscreen agents) and/or ultraviolet light absorbers. In certain embodiments, the cosmetic composition may include a colorant, a surfactant, a film-forming composition, and/or a rheology modifier. Suitable cosmetic compositions herein may be in any one of a variety of forms known in the art, including, for example, an emulsion, lotion, milk, liquid, solid, cream, gel, mouse, ointment, paste, serum, stick, spray, tonic, aerosol, foam, pencil, and the like. The cosmetic compositions may also be incorporated into shave prep products, including, for example, gels, foams, lotions, and creams, and include both aerosol and non-aerosol versions. Other cosmetic compositions include antiperspirant, deodorant, and personal cleaning compositions such as soap and shampoo.

Compositions incorporating test agents identified using methods described herein may be generally prepared by conventional methods such as known in the art of making compositions and topical compositions. Such methods typically involve mixing of ingredients in or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability, etc.) and/or delivery of active materials. The composition may be provided in a package sized to store a sufficient amount of the composition for a treatment period. The size, shape, and design of the package may vary widely. Certain package examples are described in USPNs D 570,707; D391, 162; D516,436; D535,191; D542,660; D547, 193; D547,661; D558,591; D563,221; 2009/0017080; 2007/0205226; and 2007/0040306.

IX. Examples

The following are non-limiting examples of various aspects of the methods described herein. The examples are given solely for the purpose of illustration and are not to be construed as limiting the invention, as many variations thereof are possible.

Example 1

Skin Preparation

Individual experiments generally comprise processing of human surgical waste skin used for related ex-vivo (explant) studies. An example embodiment is herein described below:

Materials for preparation included: Dulbecco's Modified Eagle Medium plus Glutamax, antibiotic and antimycotics, 1× phosphate buffer solution (PBS (−ca, −mg)), 150×15 mm sterile culture dishes, sterile gauze 4×4, disposable safety scalpels, 4 mm disposable biopsy punch, 6-well cell culture inserts, disinfected tweezers, cotton-Tipped Applicators, 6-well culture plates, ruled, disinfected cutting mat (12×12), scraper handle, tissue freezing medium, biopsy cassettes, frozen tissue freezing vessels, 10% formalin, shipping containers for fixed tissue, and biohazard/sharps containers.

Skin preparation involved preparation of media in advance of the arrival of skin (3× media including 500 ml DMEM plus 15 ml of antibiotic and antimycotics; The 3× referred to 3-fold levels of antibiotics/antimycotics used for the initial hour of incubation; 1× Media: 500 ml DMEM plus 5 ml of antibiotic and antimycotics). The skin arrived with the dermis (fat) side down on sterile DMEM soaked gauze in a sterile culture dish. The culture dish was taped shut and in a biohazard zip-lock baggie on an ice pack in a secondary container.

On arrival, the skin was removed from the bag and soaked in 3×DMEM media and stored at 4° C. for 1 hour. After 1 hour, the skin was removed from the 3×DMEM and rinsed with sterile 1×PBS. The skin was placed in a clean culture dish containing gauze soaked with 1×DMEM. The sample was put in culture the same day as arrival, though in certain embodiments the sample is placed at 4° C. overnight.

In preparation for culture, the following was performed: on a cutting mat the skin was flipped over so that the epidermis was down and the fat was exposed. The fat was removed with a disposable scalpel by carefully grasping one corner of the skin with sterile serrated forceps and scraping the fat away with the blade held at a 45° angle to the skin. After the fat was removed, the surgical edges were cut off with a scalpel using a scraper as a straight edge guide and to hold the skin in place. Using the scraper as a guide, the skin was cut into 1.25 cm (2×2 squares on grid) wide strips using a ruler (such as one a cutting mat) to measure the width. The strip was rinsed in a 100 mm culture dish containing 1×PBS. The strips were cut into 1.25 cm$^2$ squares and placed in a 100 mm culture dish onto 1×DMEM soaked gauze until they were put into culture 30 minutes later (with timepoints of 15 minutes, 30 minutes, 45 minutes, or an hour being used in various non-limiting examples).

Example 2

Culturing

An example embodiment of culturing using ex-vivo skin is herein described below:

Culturing involved setting up culture plates: putting 2.5 ml of media or treatment into each well of a 6-well tissue plate, adding one Millicell culture insert to each well, and putting 100 µl of 1×DMEM on the center of each insert membrane. Squares were selected randomly placed into each of the inserts (one piece of skin per insert), on top of the media on the membrane. The plates were stored at either 33° C. (though an additional non-limiting example would be 37° C. depending on the experiment endpoint). As a control, baseline tissue measurements were collected from excess waste (cryogenics were used for snap freezing). Baseline biopsy collection involved two 4 mm punches for MTT; One 4 mm punch was snap frozen in OCT for fresh histology; One 4 mm punch was fixed in 10% formalin and sent out for paraffin embedding. PCR baseline was also be taken with six 4 mm punches snap frozen in liquid nitrogen.

Culture and treatment of the model comprised replicates of n=5 (though replicates of additional quantities may be used such as n=6). Media Dosing of skin involved solubilizing used in appropriate solvents (including PBS, Media, alcohol, and DMSO; in using DMSO, the final concentration in the plate was restricted to 0.01%). Appropriate dilutions were made for treatment: 15 ml of media were required per plate per day for treatment, with 2.5 ml of media required per well under the cell culture insert. Media was pre-warmed and changed every day during the experiment.

Skin was topically dosed. To do so, formulation for a compound of interest was obtained. Variation was minimized by having a vehicle that was as close to test formula as possible (making sure glycerin concentration was the same, determining if there was a vitamin package in the formula, determining if there was niacimamide; all of these were the same between the vehicle control formula and the test formula) (in ideal embodiments, the only difference is the unknown test compound). The skin was treated using a positive displacement pipette with 20 ul of formulation. A sterile cotton swab was used after application to spread and rub in the formula. Media was changed every day. The media was aspirated and replaced with fresh warmed media at a level of 2.5 ml per well.

The culturing process involved the processes of maintaining and assessing viable cultures, and preparing in advance for the collection of tissue for mRNA analysis. These processes were prepared for using various preparation steps for viability tests and by preparing for culture end-point analysis (for timepoint experiments). An MTT colorimetric assay was utilized to assess cellular viability (MTT (3-(4, 5-Dimethylthiazol-2-yl)-2,5-diphenyltetrazolium bromide)). Cryogenics were used for sample collection.

Prior to starting experiment takedown, all tubes and plates were properly labeled. A cutting mat, forceps, 4 mm punches, a liquid nitrogen bucket, and an MTT plate setup were made available. Also, one set of tubes were acquired to obtain RNA (with in specific embodiments 6 baseline samples collected). The MTT plate was pre-labeled and 600 ul of 1 mg/ml MTT in DMEM media was added to each well. All samples were 4 mm biopsies. Using a biopsy punch (such as a Sklar 4 mm biopsy punch) and a hammer on a craft cutting mat (previously cleaned with alcohol) 2 punches for RNA were taken as well as 1 punch for MTT. The hammer was lightly tapped to take the biopsy, working with one treatment group (such as n=5 or n=6) on a mat at a time to take all necessary punches. Two punches were placed in a screw cap tube and snap frozen in liquid nitrogen. One punch was placed per well in an MTT plate. Work was performed quickly; time per treatment group to collect all samples was 5 minutes (with 5-10 minutes being non-limiting examples of time for collection). Once all groups were processed, the MTT plate was placed in an incubator for 24 hrs.

The MTT assessment involved 24 hours of incubation in an incubator. Well plates (2 ml deep) were provided with 1 ml of isoropanol per sample. One sample was placed per well, and the well was sealed and labeled. The plates were placed in 4° C. for 3 days of extraction (samples must extract for at least 3 days before reading, though longer extraction is conceived of in certain embodiments).

The MTT plate was read in the following manner: a 96 well clear flat bottom plate was used (though any cell culture plate can conceivably be used). Isopropanol was mixed in the deep well plate, after which 150 ul of each sample was pipetted into the new 96 well plate. An EPOCH plate reader with GENS software was used, and an absorbance endpoint was chosen for use (at 562 in one example). The plate was placed in the reader and a reading was taken. Data was exported to an Excel sheet for manipulation and use.

Example 3 mRNA Processing, Nanodrop-Quantification and Purity Assessment, RNA Quantification Gel Protocol, cDNA Synthesis. And PCR Setup mRNA Processing mRNA was processed for the ex-vivo skin methods. An example embodiment is herein described below:

For cryopreparation and extraction the following equipment was obtained and prepared: 2 ml round bottom tubes were prepared with 1 ml of TRIZOL as was a 5 mm stainless steel bead for each sample; a dry ice bucket was obtained and liquid nitrogen was placed in the bucket. Biopsy punches were maintained on dry ice, and samples remained frozen. Cryobags and covaris cryoprep were used in freeze fracturing of samples. To freeze fracture the samples, biopsies were placed in a cryo bag (2 per sample) and dipped in liquid nitrogen, then placed in cryoprep (setting 4). The sample bag was taken out and dipped back into nitrogen. A flattened disk was removed and placed into corresponding 2 ml tubes with TRIZOL. The disk was kept frozen in the TRIZOL. The tube was closed and snap frozen, and the whole tube was placed in liquid nitrogen. After repeating the process with all the samples, samples were placed into boxes and stored at −80 until the next step.

Before thawing the samples, a PLG Heavy Tube was prepared (Pre-Spun at 12000 rpm for 2 min) prepared (working with 24 samples at a time). Frozen round bottom tubes containing samples were thawed. The samples were bead-beat for 3-minutes at 3000 rpm. Samples were centrifuge for 10-minutes at 12000 rpm. During this time tubes were set up containing 200 ul chloroform in 1.5 ml tubes. The TRIZOL supernatant was taken and added to a cholorform tube, then vortexed (15 seconds). A total of 1.2 ml was added of Supernatant and chloroform to the PLG Tube. Samples were centrifuged for 10-minutes at 12000 rpm. The aqueous phase was removed from the PLG tube to 2 ml deep wells, and each set of 24 was collected in the same plate for storing at 4 degrees between additions (in various embodiments the plate can be frozen if the sample is not placed on the Magmax the same day).

Next, a Magmax magnetic bead RNA extraction was performed. Deepwell plate containing aqueous phase were thawed. Plates were set up as shown in Table 3 shown below. A check was made of the wash buffers to ensure that the buffers had the appropriate alcohol amount added to the bottle. A modified wash 1 was used in order to obtain micro RNA extraction (12 ml in bottle plus 12 ml Isopropyl Alcohol). A second wash was also performed. Elution buffer was pre-made and did not need any additions.

TABLE 3

Machine configuration MME-96 DW Magnetic Head/4388435
Tip Comb/Cat# MME-96 DW Tip Comb/4388487
Sample Volume (ul) 500

| Plate Position | | Reagents addition Order and Usage | | Plate to Use |
|---|---|---|---|---|
| 1 | Lysis/Binding | Bead Mix | 10 ul | MME-96 DW |
| | | Sample | 500 ul | Plate/4388476 |
| | | 2-propanol | 440 ul | |
| 2 | Modified wash 1 | wash solution 1 | 300 ul | |
| 3 | 1st Wash 2 | Wash Soln 2 | 450 ul | |
| 4 | 2nd Wash 2 | Wash Soln 2 | 450 ul | |
| 5 | Elution | Elution Buffer | 90 ul | MME-96 Standard |
| 6 | Tip Comb Plate | Deep Well Tip Comb in Plate | | Plate/4388475 |

Once the plates were setup for the Magmax, the machine was turned on, the appropriate protocol was selected, and the plates were loaded. A 35 minute run cycle was performed and the plates were removed, as the investigators realized the extraction was a heated step and extra time on the extraction place would degrade RNA. The elution plate was sealed with foil and a lid was placed over the foil. RNA was stored at −80 until needed.

Nanodrop-Quantification and Purity Assessment

A nanodrop-quantification and purity assessment was performed. The elution plate containing RNA was thawed completely before doing the Nanodrop reading. The EPOCH plate reader was turned on and get the TAKE3 accessory plate was taken out and placed in the reader. Slides were cleaned with water then alcohol before use, between samples and before putting away. The Gen5 software was opened, and a TAKE3 session selected, selecting nanodrop for the sample type. 3 ul of elution buffer was placed using a multichannel pipet on both columns of the slide. The accessory was closed gently. Read blanks were selected on the software. Slides were cleaned. 3 ul of sample was added to each column. Read was selected for the samples, and the software automatically exported the data to Excel. Results were exported and saved.

RNA Quantification Gel Protocol

An RNA quantification gel was performed, using Agilent Chip RNA-Nano. Reagents were prepared; the following Agilent reagents were removed from the 4° C. fridge: Agilent Blue (Dye), Agilent Yellow (Nano ladder, before use heated for 2 min at 70°, placed on ice, aliquoted in 5 ul into tubes and stored in −20°, Agilent Green, and Agilent Red (gel). Reagents were allowed to warm up to room temperature for 10 minutes. Pipetting of 550 µl Agilent Red (Gel) was performed into a filter column and centrifuged for 10 minutes at 1500 g at room temperature. Agilent Blue (Dye) was vortexed for 10 seconds. 65 µl of filtered gel was aliquotted into a tube, 1 µl of Agilent Blue (Dye) was added, and the tube was centrifuged at 13000 g for 10 minutes. Next an Agilent chip was loaded into the priming station along with 9 µl of Gel-Dye Mix. The priming station was closed for 30 seconds and the plunger was subsequently pulled. The priming station was loaded with 9 µl of Gel-Dye mix into the remaining 2 G-Wells. Regarding loading of the ladder samples, the following was used: Pipetting of 5 µl of Agilent Green into each of the wells being used, including the ladder well (in unused wells, 6 µl was added of Agilent Green), 1 µl of Agilent Yellow (Nano Ladder) was added into the Ladder Well, 1 µl of sample was added into each well; vortexing in a chip shaker was performed for 1 minute, upon which an Agilent Analyzer was used.

cDNA Synthesis

From the mRNA samples, cDNA was synthesized. cDNA reactions were made in a 0.2 ml PCR strip tube with mastermix first then sample volume and finally water. Lids were closed, and mixing and spin-downs were performed. Tubes were placed in a thermal cycler, a run was performed, and samples were held at 4 degrees; then subsequently stored at −20 until need for a PCR reaction.

PCR Setup

PCR was performed using Quanta Perfecta Sybr green master mix with ROX. PCR plates were number coded for the project. All plates came pre-plated with the primers needed for PCR. Reagents were mixed, then the reaction mixture was aliquoted across the plates putting 20 ul per well. Plate setup was 12×8, 8 samples down the plate and 12 genes across. Setup reactions was in 0.5 ml tubes. PCR plates were at room temperature before use. Mastermix was centrifuged before use. PCR analysis involved StepOne software and use of housekeeping genes and geometric means.

Example 4

Driving Tone with Endothelin

In example embodiments, tone is driven by application of stem cell factor and/or endothelin (with skin preparation, culturing, and mRNA processing being completed as previously described). In an example embodiment, skin samples are placed within 6-well plates, with 2.5 ml of media per well. A concentration of eighty nanograms per milliliter of stem cell factor as well as eighty nanograms per milliliter of endothelin was applied to tissue in the wells, with the media being refreshed daily. The culture was maintained for seven days. Inhibitors of tone-related genes were applied; hexamidine and undecylenoyl phenylalanine were applied topically and daily in vehicles at 0.1% and 0.25%, respectively.

Example 5

Driving Tone with Ultraviolet Light (UV)

The investigators have utilized UV treatment to drive tone. An example embodiment is herein described below.

Skin was obtained and cultured as previously described. Skin was treated with a dose range of UV and a time course was performed to examine UV driven regulation of the pigmentation machinery. To apply the UV treatment, the plates were placed within a solar stimulator providing UVA and UVB rays. Specifically skin was treated with 0, 1, 2, 4, and 6 J; tissue was harvested for PCR at 5 and 24 hours. Samples were carried out to 24 as well as to 96 hours. 2 & 6 J UV treatment up-regulated POMC, MC1R, MITF, Tyr, TRP2, and ENDO 1 in explant system. Using the lower dose of 2 J but waiting until 96 hours post UV produced a dramatically higher fold change in these genes as well as a 2 fold increase in DCT (dopachrome tautomerase (TYRP2)) not seen previously. In addition, the growth factors FGF2 and HGF were up-regulated in this condition as well as Endothelin receptor B. Lastly at 96 hours BCL2 (which protects against apoptosis), was up almost 3 fold whereas Bax (an apoptosis marker) was not up-regulated.

Example 6

Agents Identified by Screening Method and In Vitro and In Vivo Data from Identified Agents The ex-vivo screening method has provided identification of agents consistent with in-vitro studies and which have proven positive clinically. One such example is hexyldecanol. Hexyldecanol showed promise as an agent capable of modifying tone when tested with in-vitro models. For example, total melanin assays were performed using a rat melanoma line known to produce melanin. Hexyldecanol decreased total melanin produced by such cell cultures as compared to controls. The ex-vivo model confirmed these results (See FIGS. 25a and 25b for ex-vivo data showing down-regulation). Therefore, promising tone agents such as hexyldecanol identified from the in-vitro model and the ex-vivo model have been tested in clinical settings.

For example, hexyldecanol was compared to vehicle controls and positive controls (5% Niacinamide+1% undecylenoyl phenylalanine) through a 9-week period. Specifically the trial included a 9-week clinical study with a randomized, double-blind, round robin, vehicle-controlled, split-face design, including one week normalization period whereby 330 subjects received test product. New compound treatments were considered significantly different if p-values <0.10 (1-sided) vs. vehicle. Hexyldecanol was statistically better than vehicle controls. This agent proved significantly different from controls in spot area fraction (total area of spots per face was decreased versus the control group) and melanin evenness versus the vehicle control.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

The present invention should not be considered limited to the specific examples described herein. Various modifications, equivalent processes, as well as numerous structures and devices to which the present invention may be applicable will be readily apparent to those of skill in the art. Those skilled in the art will understand that various changes may be made without departing from the scope of the invention, which is not considered limited to what is in the specification.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A screening method for identifying a test agent as a potential skin tone agent, comprising:
   culturing a first human skin tissue sample at a temperature of 33° C. to 37° C., the first human skin tissue sample being obtained only from a human donor rated from II to IV on the Fitzpatrick Scale and comprising an epidermal layer and a dermal layer;
   contacting the first human skin tissue sample with the test agent;
   generating a transcriptional profile from the first human skin tissue sample, wherein the transcriptional profile comprises data related to transcription of at least two genes selected from propriomelancortin (POMC), melanocortin 1 receptor (MC1R), microphthalmia-associated transcription factor (MITF), tyrosinase (TYR), tyrosine related protein 1 (TYRP1), dochrachrome tautaomerase (DCT), transforming growth factor 1 (TGFB1), and endothelin 1 (END1); and identifying the test agent as a potential skin tone agent when the at least two genes show a decrease in expression level with a statistical significance of $p<0.1$ in comparison to a control.

2. The screening method of claim 1, further comprising contacting a second human skin tissue sample with a benchmark tone agent to use as the control.

3. The screening method of claim 2, wherein at least one of the first and second human skin tissue samples is a human donor tissue sample.

4. The screening method of claim 3, further comprising removing a subcutaneous fat layer from the human donor tissue sample.

5. The screening method of claim 2, wherein the benchmark tone agent down regulates, in the second human skin tissue sample, the expression level of the at least 2 genes.

6. The screening method of claim 1, wherein the first human skin tissue sample is cultured at a temperature between 30° C. and 40° C. at a relative humidity between 50% and 90% for a period 24 hours and 10 days.

7. The screening method of claim 1, wherein the first human tissue sample is stored from about 4° C. to about 10° C. prior to culturing.

8. The screening method of claim 1, further comprising placing the sample dermis-side down in an iso-osmotic solution to keep the dermis moist and the epidermis dry.

9. The screening method of claim 1, further comprising subjecting the first human skin tissue sample to one of an energy source or one or more compounds to mimic a skin tissue phenotype.

10. The screening method of claim 1, further comprising contacting the first human skin tissue sample with a paracrine agent either in a media or as applied topically.

11. The screening method of claim 1, further comprising formulating a cosmetic skin care composition comprising the test agent.

12. The screening method of claim 1, wherein the screening method is part of a tiered assay in which the test agent is subjected to at least one of an enzyme assay, a cell culture assay, and a skin equivalent assay prior to applying the test agent to the first human skin tissue sample.

13. The screening method of claim 1, further comprising changing a pigment level in the first human skin tissue sample by contacting the ex-vivo human skin tissue sample with at least one agent selected from the group consisting of Endothelin 1, Stem Cell Factor, Melanocyte Stimulating Hormone, Dobutamine, Forskolin, and ultraviolet light.

14. The screening method of claim 1, wherein the first human skin tissue sample is cultured at a temperature of about 37° C.

15. The screening method of claim 1, wherein the first human skin tissue sample is cultured at a humidity of about 50% to about 70%.

* * * * *